(12) United States Patent
Oestergaard et al.

(10) Patent No.: US 9,062,115 B2
(45) Date of Patent: Jun. 23, 2015

(54) THERAPEUTIC FACTOR VIII ANTIBODIES

(75) Inventors: Henrik Oestergaard, Oelstykke (DK); Ida Hilden, Vanloese (DK); Heidi Lindgreen Holmberg, Oelsted (DK); Kasper Lamberth, Stenloese (DK); Jes Thorn Clausen, Hoeng (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/822,952

(22) PCT Filed: Sep. 15, 2011

(86) PCT No.: PCT/EP2011/065986
§ 371 (c)(1),
(2), (4) Date: Jun. 26, 2013

(87) PCT Pub. No.: WO2012/038315
PCT Pub. Date: Mar. 29, 2012

(65) Prior Publication Data
US 2013/0266576 A1   Oct. 10, 2013

Related U.S. Application Data

(60) Provisional application No. 61/386,783, filed on Sep. 27, 2010.

(30) Foreign Application Priority Data
Sep. 22, 2010   (EP) .................................... 10178292

(51) Int. Cl.
C12P 21/08   (2006.01)
C07K 16/36   (2006.01)
C07K 16/40   (2006.01)
A61K 39/395   (2006.01)
A61K 38/37   (2006.01)

(52) U.S. Cl.
CPC ............. *C07K 16/36* (2013.01); *C07K 2317/92* (2013.01); *C07K 2317/34* (2013.01); *A61K 38/37* (2013.01); *A61K 39/3955* (2013.01)

(58) Field of Classification Search
None
See application file for complete search history.

(56) References Cited

U.S. PATENT DOCUMENTS

2005/0147618 A1   7/2005   Rivera et al.
2009/0297503 A1   12/2009   Takeyama et al.

FOREIGN PATENT DOCUMENTS

WO   2008/077616 A1   7/2008

OTHER PUBLICATIONS

Gale et al., Journal of Thrombosis and Haemostasis, "An Engineered Interdomain Disulfide Bond Stabilizes Human Blood Coagulation Factor VIIIA", 2003, vol. 1, pp. 1966-1971.
Ansong et al, Journal of Thrombosis and Haemostasis, "Epitope Mapping Factor VIII A2 Domain by Affinity-Directed Mass Spectrometry: Residues 497-510 and 584-593 Comprise a Discontinuous Epitope for the Monoclonal Antibody R8B12", 2006, vol. 4, No. 4, pp. 842-847.

(Continued)

*Primary Examiner* — Marianne P Allen
(74) *Attorney, Agent, or Firm* — Nonna G. Akopyan; Reza Green; Richard W. Bork

(57) ABSTRACT

The present invention relates to therapeutic FVIII antibodies. In particular, the present invention relates to FVIII antibodies having the ability to prolong the circulatory half life of FVIII. The present invention furthermore relates to use of such antibodies in treatment and prophylaxis of haemophilia A.

12 Claims, 11 Drawing Sheets

(56) References Cited

OTHER PUBLICATIONS

Gale et al., Journal of Thrombosis and Haemostasis, "Intrinsic Stability and Functional Properties of Disulfide Bond-Stabilized Coagulation Factor VIIIA Variants", 2006, vol. 4, pp. 1315-1322.

Green et al, British Journal of Haematology, "Haemophilia a Mutations in the UK: Results of Screening One-Third of the Population", 2008, vol. 143, pp. 115-128.

Lollar et al, Journal of Biological Chemistry, "Coagulant Properties of Hybrid Human/Porcine Factor VIII Molecules", 1992, vol. 267, No. 33, pp. 23652-23657.

Pipe et al, Proceedings of the National Academy of Sciences of the USA, "Characterization of a Genetically Engineered Inactivation-Resistant Coagulation Factor VIIIA", 1997, vol. 94, pp. 11851-11856.

Philip J. Fay, Blood Reviews, "Activation of Factor VIII and Mechanisms of Cofactor Action", 2004, vol. 18, pp. 1-15.

Radtke, K.P. et al, Journal of Thrombosis and Haemostasis, "Disulfide Bond-Stabilized Factor VIII Has Prolonged Factor VIIIA Activity and Improved Potency in Whole Blood Clotting Assays", 2007, vol. 5, No. 1, pp. 102-108.

Takeyama, M. et al, Thrombosis and Haemostasis, "Characterisation of an Antibody Specific for Coagulation Factor VIII That Enhances Factor VIII Activity", 2010, vol. 103, No. 1, pp. 94-102.

Parker et al, A1 Subunit-mediated Regulation of Thrombin-activated Factor VIII A2 Subunit Dissociation Journal :The Journal of Biological Chemistry,Year May 19, 2006, vol. 281, No. 20, pp. 13922-13930.

Fay et al, Model for the Factor VIIIa-dependent Decay of the Intrinsic Factor Xase, Journal :The Journal of Biological Chemistry, Year 1996, vol. 271, pp. 6027-6032.

Rudikoff et al.Single amino acid substitution altering antigen-binding specificity, Journal PNAS Year 1982, vol. 79, pp. 1979-1983.

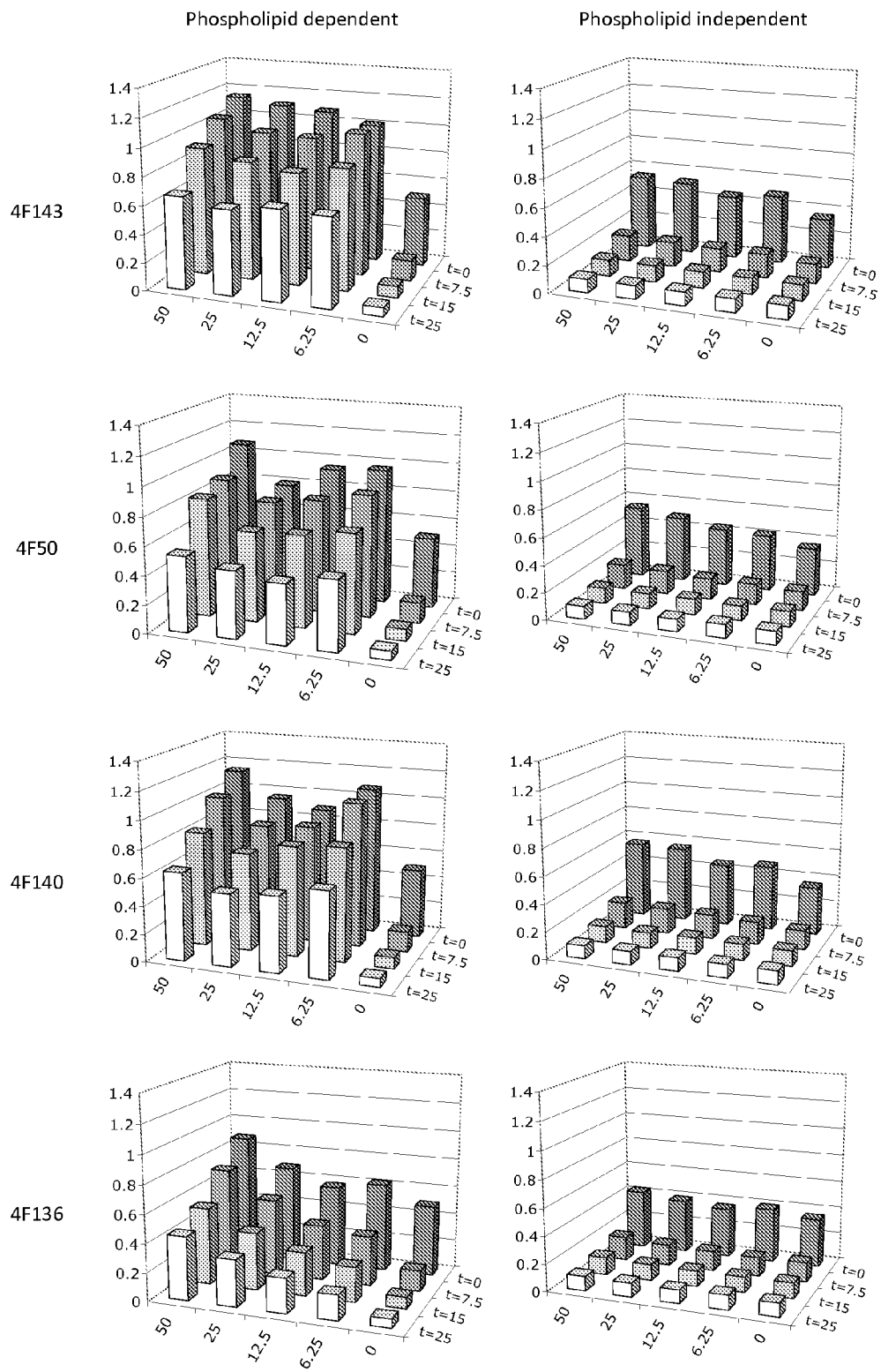

THERAPEUTIC FACTOR VIII ANTIBODIES

CROSS-REFERENCE TO RELATED APPLICATIONS

This application is a 35 U.S.C. §371 National Stage application of International Application PCT/EP2011/065986 (WO 2012/038315), filed Sep. 15, 2011, which claimed priority of European Patent Application 10178292.8, filed Sep. 22, 2010; this application claims priority under 35 U.S.C. §119 of U.S. Provisional Application 61/386,783; filed Sep. 27, 2010.

FIELD OF THE INVENTION

The present invention relates to treatment of haemophilia A. In particular, the present invention relates to therapeutic Factor VIII antibodies as well as use of Factor VIII antibodies for treatment of haemophilia A.

In accordance with 37 C.F.R. §1.52(e)(5), Applicants enclose herewith the Sequence Listing for the above-captioned application entitled "SEQUENCE LISTING", created on Mar. 5, 2013. The Sequence Listing is made up of 30 kilobytes, and the information contained in the attached "SEQUENCE LISTING" is identical to the information in the specification as originally filed. No new matter is added.

BACKGROUND OF THE INVENTION

Haemophilia A is an inherited bleeding disorder caused by deficiency or dysfunction of coagulation factor VIII (FVIII) activity. The clinical manifestation is not on primary haemostasis—formation of the blood clot occurs normally—but the clot is unstable due to a lack of secondary thrombin formation.

Haemophilia A is currently treated by intravenously injection of coagulation factor FVIII which is either isolated from blood or produced recombinantly. Treatment can be either on-demand or prophylactic. Recent published data support that prophylaxis has significant advantages over on-demand treatment. These include reduction in bleeding frequency and lower risk of developing haemophilic arthropathy, both resulting in a better quality of life for the patients. However, while prophylaxis enables a virtually symptom-free life for the patients, it requires frequent injections in a peripheral vein, typically three times a week, which is known to be painful, difficult, and time consuming. In addition, repeated venipuncture is not always possible in young children. Consequently, a product supporting less frequent administration and/or administration via a more convenient and safe route such as e.g. subcutaneous administration, would to a greater extent enable regular prophylactic treatment.

A FVIII antibody having the ability to enhance the activation of wt FVIII is disclosed in US20090297503. This antibody, however, is also shown to impair binding of wt FVIII to vWF. Impairment of FVIII:vWF binding is generally believed to be undesirable as the circulatory half life of Factor VIII is many fold higher upon vWF binding.

There is thus a need in the art for therapies that support infrequent administration and/or is capable of enhancing the activity of endogenous FVIII, and consequently the procoagulant response, in patients suffering from haemophilia A. Patients with endogenous FVIII include haemophilia A patients suffering from the mild to moderate form and a certain fraction of the severe patients.

SUMMARY OF THE INVENTION

The present invention relates to a monoclonal Factor VIII antibody having the ability to bind to activated human Factor VIII, wherein said antibody, upon binding to activated Factor VIII, reduces or inhibits dissociation of the A2 domain, and wherein said antibody does not interfere with vWF binding. The present invention furthermore relates to therapeutic use of such molecules.

Such antibodies may be useful for prolonging the lifetime of the FVIIIa/FIXa complex resulting in more thrombin being generated and consequently improved clot formation. Such antibodies are thus suitable for treatment of patients suffering from haemophilia A and not completely devoid of endogenous FVIII such as patients with mild and moderate haemophilia A and a subset of patients having severe haemophilia A. Optionally such antibodies may be used in combination with Factor VIII replacement therapy.

DESCRIPTION OF THE INVENTION

Definitions

Figure 1:
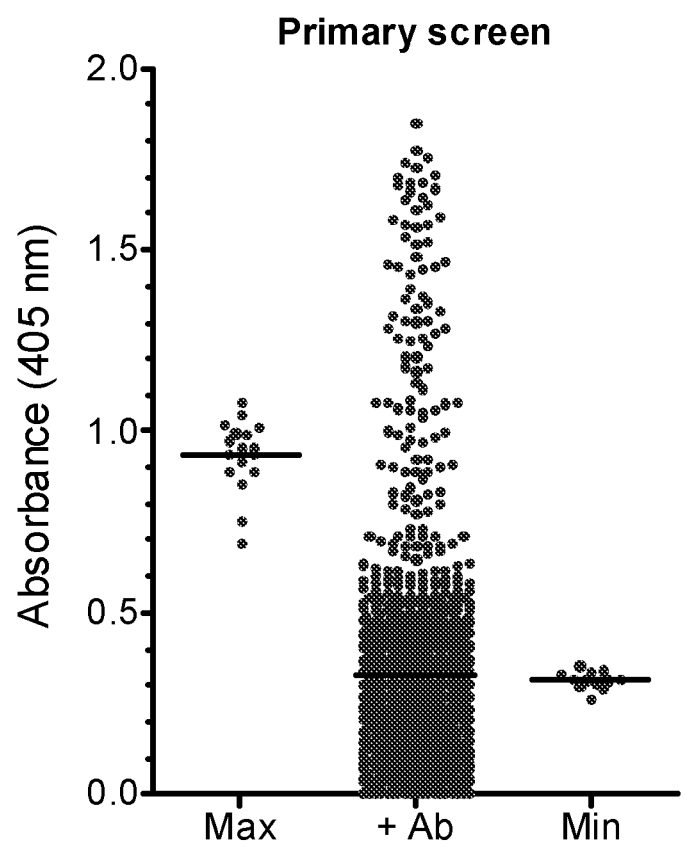
FIG. 1 shows result from the functional chromogenic primary screening assay. One medium control with no disassociation time (Max) and a medium control with a 7.5-min dissociation time (Min) defined the assay window. Several of the samples inhibited FVIII activity evidenced by activities below Min in the assay. Interestingly, a significant fraction of the samples were able to stabilize FVIII to a greater extent than the control with no dissociation time (Max).

Factor VIII antibody: Factor VIII antibodies according to the present invention have the ability to bind to activated Factor VIII and they furthermore preferably have the ability to bind to Factor VIII both before and after thrombin activation. The antibodies according to the invention may furthermore have the ability to bind to modified Factor VIII variants such as e.g. Factor VIII molecules conjugated with one or more side groups. Antibodies according to the invention may furthermore have the ability to bind to fusion proteins comprising Factor VIII and optionally conjugated with side groups. Antibodies according to the invention may furthermore have the ability to bind to Factor VIII variants comprising amino acid deletions, substitutions and/or additions such as those found in haemophilia A patients or e.g. B domain truncated/deleted Factor VIII, Factor VIII with decreased ability to bind to vWF, Factor VIII variants with modified ability to bind to various molecules (such as e.g. LRP), optionally conjugated with side groups and optionally being part of a fusion protein. Antibodies according to the present invention may in other words bind to any Factor VIII variant having Factor VIII activity. Antibodies according to the present invention may typically have a circulatory half life that is significantly longer compared to the circulatory half life of wt FVIII. Antibodies according to the invention can furthermore be administered e.g. subcutaneously which is an administration form that is usually more convenient and easy to use than IV administration.

The term "antibody" or "Factor VIII antibody", as used herein, is intended to refer to immunoglobulin molecules and fragments thereof that have the ability to specifically bind to Factor VIII and/or FVIIIa. Full-length antibodies comprise four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyterminus in the following order: FR1, CDR1, FR2, CDR2, FR3, CDR3, FR4. Thus, within the definition of an antibody according to the invention is also one or more fragments of an antibody that retain the ability to specifically bind to Factor VIII. It has been shown that the antigen-binding function of an antibody can be performed by fragments of a full-length antibody. Examples of binding fragments encompassed within the term "antibody" include (i) a Fab fragment, a monovalent fragment consisting of the VL, VH, CL and CH I domains; (ii) F(ab)2 and F(ab')2 fragments, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426: and Huston et al. (1988) Proc. Natl. Acad. Sci. USA 85:5879-5883). Such single chain antibodies are also intended to be encompassed within the term "Factor VIII antibody" according to the present invention. Other forms of single chain antibodies, such as diabodies are also encompassed in the term "Factor VIII antibody". Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Hol-liger, P., et al. (1993) Proc. Natl. Acad. Sci. USA 90:6444-6448; Poljak, R. J., et al. (1994) Structure 2:1121-1123).

The terms "human antibody", "human antibodies", as used herein, means Factor VIII antibodies according to the invention having variable and constant regions derived from human germline immunoglobulin sequences. The human Factor VIII antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3.

The term "humanized antibody" in this context refers to CDR sequences from a Facfor VIII antibody according to the invention that have been grafted onto a human scaffold. Factor VIII antibodies according to the present invention may thus be e.g. human antibodies or humanized antibodies.

The term "epitope" as used herein means any antigenic determinant on an antigen to which the antibody binds. Epitopic determinants usually consist of chemically active surface groupings of molecules such as amino acids or sugar side chains and usually have specific three dimensional structural characteristics, as well as specific charge characteristics. The terms "immunoreacts" or "immunoreacting", as used herein, means any binding of an antibody to its epitope with a dissociation constant Kd lower than 10-4 M. The terms "immunoreacts" or "immunoreacting" are used where appropriate inter-changeably with the term "specifically bind". Epitopes are often referred to as one or more regions in the amino acid sequence, and/or individual amino acid residues of the FVIII molecule that is/are covered by an antibody upon FVIII:FVIII antibody binding. Antibodies binding to a region that is overlapping e.g. with a subsection or a region of "an epitope" are also regarded as antibodies binding to this epitope as long as the antibody can be said to form non-covalent interactions with or to cover at least one, preferably at least two, more preferably at least three, more preferably at least four and most preferably at least 5-10 of the amino acids within the FVIII epitope.

The term "affinity", as used herein, means the strength of the binding of an antibody to an epitope. The affinity of an antibody is measured by the dissociation constant Kd, defined as [Ab]×[Ag]/[Ab-Ag] where [Ab-Ag] is the molar concentration of the antibodyantigen complex, [Ab] is the molar concentration of the unbound antibody and [Ag] is the molar concentration of the unbound antigen. The affinity constant Ka is defined by 1/Kd. Preferred methods for determining Mabs specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference.

Co-administration: Factor VIII antibodies according to the invention can be co-administered together with therapeutic Factor VIII molecules that may be either derived from blood or produced using recombinant techniques. Co-administration may be performed by IV administration of a pharmaceutical formulation comprising both types of therapeutic proteins. Co-administration may also be performed by IV administration of a pharmaceutical composition comprising therapeutic Factor VIII molecules and IV or subcutaneous administration of a composition comprising Factor VIII antibodies according to the present invention. Co-administration can be done either simultaneously or with an interval of from about one minute to one month, one hour to one day, or one day to one week. Administration of antibodies according to the present invention, optionally in the form as co-administration with a FVIII molecule or FVIII variant/derivative may be performed e.g. once every day, once every week, once every second week, once every third week, or once every month.

Factor VIII molecules: FVIII/Factor VIII is a large, complex glycoprotein that primarily is produced by hepatocytes. Human FVIII consists of 2351 amino acids, including signal peptide, and contains several distinct domains, as defined by homology. There are three A-domains, a unique B-domain, and two C-domains. The domain order can be listed as NH2-A1-A2-B-A3-C1-C2-COOH. FVIII circulates in plasma as two chains, separated at the B-A3 border. The chains are connected by bivalent metal ion-bindings. The A1-A2-B chain is termed the heavy chain (HC) while the A3-C1-C2 is termed the light chain (LC).

FVIII circulates associated with von Willebrand Factor (VWF). VWF is a large multimeric glycoprotein that serves as a carrier for FVIII and is required for normal platelet adhesion to components of the vessel wall. The plasma-half life of FVIII in complex with VWF is approximately 12 hours.

FVIII is activated by thrombin or FXa by cleavages in the HC and LC, which releases FVIIIa from VWF. This process produces a heterotrimeric molecule consisting of A1 and A2 domains non-covalently linked to the A3-C1-C2 light chain through ionic interactions. The FVIIIa molecule is inherently unstable as a consequence of spontaneous A2 subunit dissociation and concomitant loss of cofactor activity (References: Fay (1991) JBC, 266:8957-8962; Lamphear (1992) JBC, 267:3725-3730; Fay (1992) JBC 267:13246-13250; Fay (1993) JBC 268:17861-17866; Fay (1996) JBC 271:6027-6032; Parker (2007) JBC 281:13922-13930; Parker (2007) Biochemistry 46:9737-9742). Dissociation occurs with a half-life of approximately 2 min and appears to be the predominant physiological mechanism for down-regulation of the FVIIIa/FIXa complex (Fay P J (2004) Blood Reviews, 18:1-15). FVIIIa can also be inactivated by the anticoagulant serine protease, activated protein C (APC) which cleaves FVIIIa at additional site in the heavy chain. However, the physiological relevance of this pathway appears to be minor (Fay P J (2004) Blood Reviews, 18:1-15).

"Native FVIII" is the full length human FVIII molecule as shown in SEQ ID NO. 1 (amino acid 1-2332). The B-domain is spanning amino acids 741-1648 in SEQ ID NO 1.

```
SEQ ID NO 1:
ATRRYYLGAVELSWDYMQSDLGELPVDARFPPRVPKSFPFNTSVVYKKTLFVEFT

DHLFNIAKPRPPWMGLLGPTIQAEVYDTVVITLKNMASHPVSLHAVGVSYWKASEGAEYDD

QTSQREKEDDKVFPGGSHTYVWQVLKENGPMASDPLCLTYSYLSHVDLVKDLNSGLIGALL

VCREGSLAKEKTQTLHKFILLFAVFDEGKSWHSETKNSLMQDRDAASARAWPKMHTVNGY

VNRSLPGLIGCHRKSVYWHVIGMGTTPEVHSIFLEGHTFLVRNHRQASLEISPITFLTAQTLL

MDLGQFLLFCHISSHQHDGMEAYVKVDSCPEEPQLRMKNNEEAEDYDDDLTDSEMDVVRF

DDDNSPSFIQIRSVAKKHPKTWVHYIAAEEEDWDYAPLVLAPDDRSYKSQYLNNGPQRIGR

KYKKVRFMAYTDETFKTREAIQHESGILGPLLYGEVGDTLLIIFKNQASRPYNIYPHGITDVRP

LYSRRLPKGVKHLKDFPILPGEIFKYKWTVTVEDGPTKSDPRCLTRYYSSFVNMERDLASGLI

GPLLICYKESVDQRGNQIMSDKRNVILFSVFDENRSWYLTENIQRFLPNPAGVQLEDPEFQA

SNIMHSINGYVFDSLQLSVCLHEVAYWYILSIGAQTDFLSVFFSGYTFKHKMVYEDTLTLFPF

SGETVFMSMENPGLWILGCHNSDFRNRGMTALLKVSSCDKNTGDYYEDSYEDISAYLLSKN

NAIEPRSFSQNSRHPSTRQKQFNATTIPENDIEKTDPWFAHRTPMPKIQNVSSSDLLMLLRQ

SPTPHGLSLSDLQEAKYETFSDDPSPGAIDSNNSLSEMTHFRPQLHHSGDMVFTPESGLQL

RLNEKLGTTAATELKKLDFKVSSTSNNLISTIPSDNLAAGTDNTSSLGPPSMPVHYDSQLDTT

LFGKKSSPLTESGGPLSLSEENNDSKLLESGLMNSQESSWGKNVSSTESGRLFKGKRAHG

PALLTKDNALFKVSISLLKTNKTSNNSATNRKTHIDGPSLLIENSPSVWQNILESDTEFKKVTP

LIHDRMLMDKNATALRLNHMSNKTTSSKNMEMVQQKKEGPIPPDAQNPDMSFFKMLFLPES

ARWIQRTHGKNSLNSGQGPSPKQLVSLGPEKSVEGQNFLSEKNKVVVGKGEFTKDVGLKE

MVFPSSRNLFLTNLDNLHENNTHNQEKKIQEEIEKKETLIQENVVLPQIHTVTGTKNFMKNLF

LLSTRQNVEGSYDGAYAPVLQDFRSLNDSTNRTKKHTAHFSKKGEEENLEGLGNQTKQIVE

KYACTTRISPNTSQQNFVTQRSKRALKQFRLPLEETELEKRIIVDDTSTQWSKNMKHLTPSTL

TQIDYNEKEKGAITQSPLSDCLTRSHSIPQANRSPLPIAKVSSFPSIRPIYLTRVLFQDNSSHL

PAASYRKKDSGVQESSHFLQGAKKNNLSLAILTLEMTGDQREVGSLGTSATNSVTYKKVEN

TVLPKPDLPKTSGKVELLPKVHIYQKDLFPTETSNGSPGHLDLVEGSLLQGTEGAIKWNEAN

RPGKVPFLRVATESSAKTPSKLLDPLAWDNHYGTQIPKEEWKSQEKSPEKTAFKKKDTILSL

NACESNHAIAAINEGQNKPEIEVTWAKQGRTERLCSQNPPVLKRHQREITRTTLQSDQEEID

YDDTISVEMKKEDFDIYDEDENQSPRSFQKKTRHYFIAAVERLWDYGMSSSPHVLRNRAQS

GSVPQFKKVVFQEFTDGSFTQPLYRGELNEHLGLLGPYIRAEVEDNIMVTFRNQASRPYSFY

SSLISYEEDQRQGAEPRKNFVKPNETKTYFWKVQHHMAPTKDEFDCKAWAYFSDVDLEKD

VHSGLIGPLLVCHTNTLNPAHGRQVTVQEFALFFTIFDETKSWYFTENMERNCRAPCNIQME

DPTFKENYRFHAINGYIMDTLPGLVMAQDQRIRWYLLSMGSNENIHSIHFSGHVFTVRKKEE

YKMALYNLYPGVFETVEMLPSKAGIWRVECLIGEHLHAGMSTLFLVYSNKCQTPLGMASGHI

RDFQITASGQYGQWAPKLARLHYSGSINAWSTKEPFSWIKVDLLAPMIIHGIKTQGARQKFS

SLYISQFIIMYSLDGKKWQTYRGNSTGTLMVFFGNVDSSGIKHNIFNPPIIARYIRLHPTHYSIR

STLRMELMGCDLNSCSMPLGMESKAISDAQITASSYFTNMFATWSPSKARLHLQGRSNAW

RPQVNNPKEWLQVDFQKTMKVTGVTTQGVKSLLTSMYVKEFLISSSQDGHQWTLFFQNGK

VKVFQGNQDSFTPVVNSLDPPLLTRYLRIHPQSWVHQIALRMEVLGCEAQDLY
```

"Factor VIII molecules" that are co-administrated along with Factor VIII antibodies according to the present invention may be Factor VIII isolated from blood plasma and/or recombinant Factor VIII. Factor VIII molecules to be coadministrated together with the Factor FVIII antibodies according to the invention may be e.g. B domain truncated Factor FVIII molecules wherein e.g. the remaining domains correspond closely to the sequence as set forth in amino acid no 1-740 and 1649-2332 in SEQ ID NO. 1 (although there may also e.g. be one or more alterations within the vWF binding region between residues 1670-1684). B domain truncated molecules co-administered with Factor VIII antibodies according to the invention may differ slightly from the sequence set forth in SEQ ID NO 1, meaning that the remaining domains (i.e. the three A-domains and the two C-domains) may differ slightly e.g. 1, 2, 3, 4, 5, 6, 7, 8, 9, or 10 amino acids, alternatively may differ about 1%, 2%, 3%, 4% or 5% from the amino acid sequence as set forth in SEQ ID NO 1 (amino acids 1-740 and 1649-2332) due to the fact that mutations can be introduced in order to e.g. reduce vWF binding capacity. Furthermore, it is plausible that amino acid modifications (substitutions, deletions, etc.) are introduced other places in the molecule in order to modify the binding capacity of Factor VIII with various other components such as e.g. LRP, various receptors, other coagulation factors, cell surfaces, introduction and/or abolishment of glycosylation sites, etc.

Factor VIII molecules that are co-adminstered along with Factor VIII antibodies according to the present invention have Factor VIII activity, meaning the ability to function in the coagulation cascade in a manner functionally similar or equivalent to FVIII, induce the formation of FXa via interaction with FIXa on an activated platelet, and support the formation of a blood clot. The activity can be assessed in vitro by techniques well known in the art such as e.g. clot analysis, endogenous thrombin potential analysis, etc. Factor VIII molecules co-adminstered with Factor VIII antibodies according to the invention have FVIII activity being at least about 10%, at least 20%, at least 30%, at least 40%, at least 50%, at least 60%, at least 70%, at least 80%, at least 90%, and 100% or even more than 100% of that of native human FVIII.

Reduction/Inhibition of dissociation of the A2 subunit refers to the situation where the rate of dissociation of the A2 subunit from activated FVIII is reduced as compared to e.g. the rate of dissociation of wtFVIII (optionally in the presence of a control antibody) as measured in the presence of antibody and e.g. 5, 10, 15, 20, or 25 minutes after activation of FVIII to FVIIIa. Antibodies according to the present invention result in a reduction of dissociation of the A2 domain of 10% or more, preferably 15% or more, more preferably 20% or more, more preferably 25% or more, more preferably 30% or more, more preferably 35% or more, more preferably 40% or more, more preferably 45% or more, more preferably 50% or more, more preferably 55% or more, more preferably 60% or more, more preferably 65% or more, more preferably 70% or more, more preferably 75% or more, more preferably 80% or more, and most preferably 90% or more. Such property can be determined in a functional decay assay as described in Example 4 and elsewhere (Fay et al. (1996) JBC, 271:6027-6032; Parker et al. (2006) JBC, 281:13922-13930). The assay measures the cofactor activity of FVIIIa as a function of time following activation of FVIII by thrombin. The cofactor activity of FVIIIa is measured as its ability to stimulate the conversion of FX to FXa in the presence of a suitable phospholipid surface and factor IXa.

B Domain: The B-domain in Factor VIII spans amino acids 741-1648 in SEQ ID NO 1. The B-domain is cleaved at several different sites, generating large heterogeneity in circulating plasma FVIII molecules. The exact function of the heavily glycosylated B-domain is unknown. What is known is that the domain is dispensable for FVIII activity in the coagulation cascade. This apparent lack of function is supported by the fact that B domain deleted/truncated FVIII appears to have in vivo properties identical to those seen for full length native FVIII.

B Domain truncated/deleted Factor VIII molecule: Endogenous full length FVIII is synthesized as a single-chain precursor molecule. Prior to secretion, the precursor is cleaved into the heavy chain and the light chain. Recombinant B domain-deleted FVIII can be produced from two different strategies. Either the heavy chain without the B-domain and the light chain are synthesized individually as two different polypeptide chains (two-chain strategy) or the B-domain deleted FVIII is synthesized as a single precursor polypeptide chain (single-chain strategy) that is cleaved into the heavy and light chains in the same way as the full-length FVIII precursor.

In a B domain-deleted FVIII precursor polypeptide, the heavy and light chain moieties are normally separated by a linker. To minimize the risk of introducing immunogenic epitopes in the B domain-deleted FVIII, the sequence of the linker is preferable derived from the FVIII B-domain. As a minimum, the linker must comprise a recognition site for the protease that cleaves the B domain-deleted FVIII precursor polypeptide into the heavy and light chain. In the B domain of full length FVIII, amino acid 1644-1648 constitutes this recognition site. The thrombin site leading to removal of the linker on activation of B domain-deleted FVIII is located in the heavy chain. Thus, the size and amino acid sequence of the linker is unlikely to influence its removal from the remaining FVIII molecule by thrombin activation. Deletion/truncation of the B domain is an advantage for production of FVIII. Nevertheless, parts of the B domain can be included in the linker without reducing the productivity. The negative effect of the B domain on productivity has not been attributed to any specific size or sequence of the B domain.

B-domain truncated/deleted Factor VIII variants that can be co-administered with Factor VIII antibodies according to the invention may contain one or more O-glycosylation sites. However, according to a preferred embodiment, the molecule comprises only one O-linked oligosaccharides in the truncated B-domain—an example thereof is the BDD-FVIII 40 KDa PEG (O-glycan) molecule disclosed in FIG. 7 in WO09108806, wherein the amino acid sequence of the B domain is: SFSQNSRHPSQNPPVLKRHQR (SEQ ID NO 2). An O-linked glycan may be used for conjugating the Factor VIII molecule with various side groups as described in the methods in e.g. WO0331464.

The Factor VIII molecule that is co-administered with Factor VIII antibodies according to the invention comprises a number of N-linked oligosaccharides and each of these may likewise potentially serve as an anchor for attachment of a side group (as disclosed in e.g. WO0331464).

The length of the B domain in the wt FVIII molecule is about 907 amino acids. The length of the truncated B domain in Factor VIII molecules co-administered with Factor VIII antibodies according to the present invention may vary from about 10 to about 800 amino acids, such as e.g. from about 10 amino acids to about 700 acids, such as e.g. about 12-500 amino acids, 12-400 amino acids, 12-300 amino acids, 12-200 amino acids, 15-100 amino acids, 15-75 amino acids, 15-50 amino acids, 15-45 amino acids, 20-45 amino acids, 20-40 amino acids, or 20-30 amino acids. The truncated B-domain may comprise fragments of the heavy chain and/or the light chain and/or an artificially introduced sequence that is not found in the wt FVIII molecule. The terms "B-domain truncated" and "B-domain deleted" may be used interchangeably herein.

Von Willebrandt Factor (vWF): vWF is a large mono-/multimeric glycoprotein present in blood plasma and produced constitutively in endothelium (in the Weibel-Palade bodies), megakaryocytes (α-granules of platelets), and subendothelial connective tissue. Its primary function is binding to other proteins, particularly Factor VIII and it is important in platelet adhesion to wound sites.

Factor VIII is bound to vWF while inactive in circulation; Factor VIII degrades rapidly or is cleared when not bound to vWF. Antibodies according to the present invention do not interfere with vWF binding to FVIII or FVIII variants. Non-interference with vWF binding is in connection with the present invention defined as a reduced binding to vWF of preferably 0%, or alternatively less than 2%, or less than 5%, or less than 10%, or less than 15%, or less than 20%, or less than 25%, or less than 30% at a concentration of antibody ensuring FVIII saturation, such as an antibody concentration 10-fold above the measured dissociation constant for the antibody-FVIII interaction. An assay that can be used to measure vWF:FVIII binding is disclosed e.g. in Example 5.

The term "reduced capacity to bind vWF" is herein meant to encompass Factor VIII variants, that are co-administered with Factor VIII antibodies according to the invention, wherein the capacity to bind vWF is decreased by at least 50%, preferably by at least 60%, more preferably by at least 70%, more preferably by at least 80%, more preferably by at least 90%, and most preferably about 100%. FVIII binding to vWF may be measured either by an solid-phase assay or as direct binding to immobilized vWF using surface plasmon resonance. The region in Factor VIII responsible for binding to vWF is the region spanning residues 1670-1684 as disclosed in EP0319315. It is envisaged that Factor VIII point and/or deletion mutants involving this area will modify the ability to bind to vWF. Examples of particularly preferred point mutations according to the present invention include variants comprising one or more of the following point mutations: Y1680F, Y1680R, Y1680N, and E1682T, and Y1680C. If the FVIII variants co-administered along with antibodies according to the invention, are modified with relation to their capacity to bind to vWF, then such FVIII variants are preferably protracted e.g. with a protracting group such as e.g. PEG, fatty acid derivates, albumin, etc.

Suitable host cells for producing antibodies according to the invention as well as recombinant factor VIII protein, that can be co-administered with Factor VIII antibodies according to the invention, are preferably of mammalian origin in order to ensure that the molecule is properly processed during folding and post-translational modification, eg. glycosylation and sulfatation. In practicing the present invention, the cells are mammalian cells, more preferably an established mammalian cell line, including, without limitation, CHO (e.g., ATCC CCL 61), COS-1 (e.g., ATCC CRL 1650), baby hamster kidney (BHK), and HEK293 (e.g., ATCC CRL 1573; Graham et al., J. Gen. Virol. 36:59-72, 1977) cell lines. A preferred BHK cell line is the tk− ts13 BHK cell line (Waechter and Baserga, Proc. Natl. Acad. Sci. USA 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk− ts13 BHK cell line is also available from the ATCC under accession number CRL 1632. A preferred CHO cell line is the CHO K1 cell line available from ATCC under accession number CCl61 as well as cell lines CHO-DXB11 and CHO-DG44.

Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1); DUKX cells (CHO cell line) (Urlaub and Chasin, Proc. Natl. Acad. Sci. USA 77:4216-4220, 1980) (DUKX cells also being referred to as DXB11 cells), and DG44 (CHO cell line) (Cell, 33: 405, 1983, and Somatic Cell and Molecular Genetics 12: 555, 1986). Also useful are 3T3 cells, Namalwa cells, myelomas and fusions of myelomas with other cells. In some embodiments, the cells may be mutant or recombinant cells, such as, e.g., cells that express a qualitatively or quantitatively different spectrum of enzymes that catalyze post-translational modification of proteins (e.g., glycosylation enzymes such as glycosyl transferases and/or glycosidases, or processing enzymes such as propeptides) than the cell type from which they were derived. DUKX cells (CHO cell line) are especially preferred.

Currently preferred cells are HEK293, COS, Chinese Hamster Ovary (CHO) cells, Baby Hamster Kidney (BHK) and myeloma cells, in particular Chinese Hamster Ovary (CHO) cells.

Modified circulatory half life: Administration of Factor VIII antibodies according to the present invention alone or in combination with therapeutic Factor VIII molecules may result in a prolonged circulatory half life of endogenous Factor VIII or a prolonged half life of endogenous Factor FVIII in combination with therapeutic Factor VIII, or a prolonged half life of therapeutic Factor VIII. Circulatory half life is preferably increased at least 10%, preferably at least 15%, preferably at least 20%, preferably at least 25%, preferably at least 30%, preferably at least 35%, preferably at least 40%, preferably at least 45%, preferably at least 50%, preferably at least 55%, preferably at least 60%, preferably at least 65%, preferably at least 70%, preferably at least 75%, preferably at least 80%, preferably at least 85%, preferably at least 90%, preferably at least 95%, preferably at least 100%, more preferably at least 125%, more preferably at least 150%, more preferably at least 175%, more preferably at least 200%, and most preferably at least 250% or 300%. Even more preferably, such molecules have a circulatory half life that is increased at least 400%, 500%, 600%, or even 700%.

Side chain/side group: Factor VIII Side groups may comprise a hydrophilic polymer such as e.g. a PEG molecule, molecules of a mainly hydrophobic nature, such as e.g. fatty acids, molecules of peptidic origin, etc. Side groups are usually conjugated to Factor VIII via a linker. Such conjugated Factor VIII molecules may be co-administered with Factor VIII antibodies according to the invention.

Pharmaceutical composition: A pharmaceutical composition is herein preferably meant to encompass compositions comprising Factor VIII antibodies according to the present invention optionally in combination with Factor VIII molecules suitable for parenteral administration, such as e.g. ready-to-use sterile aqueous compositions or dry sterile compositions that can be reconstituted in e.g. water or an aqueous buffer. The compositions according to the invention may comprise various pharmaceutically acceptable excipients, stabilizers, etc.

Additional ingredients in such compositions may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention. Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the FVIII antibody compound in the form of a nasal or pulmonal spray. As a still further option, the pharmaceutical compositions containing the FVIII compound of the invention may also be adapted to transdermal administration, e.g. by needle-free injection or from a patch, optionally an iontophoretic patch, or transmucosal, e.g. buccal, administration.

The term "treatment", as used herein, refers to the medical therapy of any human or other animal subject in need thereof. Said subject is expected to have undergone physical examination by a medical practitioner, who has given a tentative or definitive diagnosis which would indicate that the use of said specific treatment is beneficial to the health of said human or other animal subject. The timing and purpose of said treatment may vary from one individual to another, according to the status quo of the subject's health. Thus, said treatment may be prophylactic, palliative, symptomatic and/or curative.

LIST OF EMBODIMENTS

The present invention includes the following non-limiting embodiments:

Embodiment 1

A monoclonal Factor VIII antibody having the ability to bind to activated human Factor VIII, wherein said antibody, upon binding to activated Factor VIII, reduces dissociation of the A2 domain, and wherein said antibody does not interfere with vWF binding.

Embodiment 2

An antibody according to embodiment 1, wherein the reduction of A2 subunit association occurs in the absence or presence of a phospholipid surface.

Embodiment 3

An antibody according to embodiment 1, wherein the reduction of A2 subunit dissociation from the activated Factor VIII molecule is improved in the presence of a phospholipid surface.

Embodiment 4

An antibody according to embodiment 2 or 3, wherein administration of this antibody results in increased thrombin activation in the presence of platelets.

Embodiment 5

A monoclonal antibody according to any one of embodiments 1-4, wherein said antibody does not accelerate thrombin activation.

Embodiment 6

An antibody according to any one of embodiments 1-5, wherein said antibody binds to the A2 domain.

Embodiment 7

An antibody according to any one of embodiments 1-5, wherein said antibody binds to the A3 domain.

Embodiment 8

An antibody according to any one of embodiments 1-6, wherein, wherein said antibody comprises one, two, three, four, or five CDR sequences having at least 95% identity, more preferably at least 96% identity, more preferably at least 97% identity with, more preferably at least 98% identity with, more preferably at least 99% identity with, or most preferably 100% identity with one, two, three, four, or five of the CDR sequences selected from the list consisting of: SEQ ID NO: 6, SEQ ID NO 7, SEQ ID NO 8, SEQ ID NO 11, SEQ ID NO 12, and SEQ ID NO 13 or the list consisting of: SEQ ID NO 16, SEQ ID NO 17, SEQ ID NO 18, SEQ ID NO 21, SEQ ID NO 22, and SEQ ID NO 23.

Embodiment 9

An antibody according to embodiment 8, wherein the CDR sequences of said antibody have at least 95% identity, preferably at least 96% identity, preferably at least 97% identity, preferably at least 98% identity, preferably at least 99% identity, and most preferably 100% identity with the following CDR sequences: SEQ ID NO: 6, SEQ ID NO 7, SEQ ID NO 8, SEQ ID NO 11, SEQ ID NO 12, and SEQ ID NO 13 or SEQ ID NO 16, SEQ ID NO 17, SEQ ID NO 18, SEQ ID NO 21, SEQ ID NO 22, and SEQ ID NO 23.

Embodiment 10

An antibody according to any one of embodiments 8-9, wherein said antibody comprises a VL sequence having at least 95% identity, preferably at least 96%, preferably at least 97% identity, preferably at least 98% identity, and most preferably 100% identity with SEQ ID NO 10 or SEQ ID NO 20 and a VH sequence having at least 95% identity, preferably at least 96%, preferably at least 97% identity, preferably at least 98% identity, and most preferably 100% identity with SEQ ID NO 9 OR SEQ ID NO 15.

Embodiment 11

An antibody according to any one of embodiments 1-10, wherein said antibody binds to an epitope identical with or overlapping with the peptide fragment 407-428 (SEQ ID NO 15) and/or 591-602 (SEQ ID NO 16).

Embodiment 12

An antibody according to any one of embodiments 1-10, wherein said antibody binds to an epitope identical with or overlapping the peptide fragment 1965-1976 (SEQ ID NO 17).

Embodiment 13

An antibody according to any of embodiments 1-12, wherein said antibody competes with binding to the 4F143 antibody.

Embodiment 14

A DNA molecule comprising a DNA sequence encoding an antibody according to any one of embodiments 1-13. Optionally this DNA molecule is embedded in an expression vector.

Embodiment 14A

A host cell comprising the DNA molecule according to embodiment 14.

Embodiment 15

Use of an antibody according to any one of embodiments 1-13 as a medicament for treatment of haemophilia A, such as mild, moderate, or severe haemophilia A.

Embodiment 16

A pharmaceutical composition comprising an antibody according to any one of embodiments 1-13 and optionally a pharmaceutically acceptable excipient.

Embodiment 17

A pharmaceutical composition comprising an antibody according to any one of embodiments 1-13 and a Factor VIII molecule and optionally a pharmaceutically acceptable excipient. The pharmaceutical composition according to any one of embodiments 16 or 17 may be for subcutaneous administration.

Embodiment 18

A method of making an antibody according to any one of embodiments 1-13, wherein said method comprises incubation of a host cell comprising a DNA molecule encoding such antibody under conditions suitable for expressing said antibody.

Embodiment 19

A method of treatment of a haemophilic disease comprising administering to a patient in need thereof a therapeutically effective amount of a molecule according to any one of embodiments 1-13, optionally in combination with a Factor VIII molecule. The molecule according to any one of embodiments 1-13 may be in the form of a pharmaceutical composition according to embodiment 16 or 17.

EXAMPLES

Proteins

B-domain deleted factor VIII (FVIII) was prepared recombinantly in chinese hamster ovary (CHO) cells as described elsewhere (Thim et al., 2010). Recombinant hirudin (Rydel et al., 1990) was cloned into pET-26b(+) (Novagen, San Diego, Calif.) and purified following periplasmic expression in *Escherichia coli* via the introduced LeuGln(His)$_6$-tag using standard nickel nitrilo-triacetic acid (Ni-NTA) chromatography.

Example 1

Antibody Production

Monoclonal antibodies (mAbs) of the present invention can be produced by a variety of techniques, including conventional monoclonal methodology e.g., the standard somatic cell hybridization technique of Kohler and Milstein (1975) Nature 256:495. Although somatic cell hybridization procedures are preferred, in principle, other techniques for production of monoclonal antibody can be employed e.g., viral or oncogenic transformation of B lymphocytes, phage display techniques using libraries of human or other species (mouse, rabbit, rat, guinea pig) antibody genes.

RBF, Balb/c, NMRICF1 or FVIII deficient mice were used for immunizations and production of mouse monoclonal antibodies. As antigen for immunization FVIII was used either preactivated with thrombin or on the pro-cofactor form. Injections were made subcutaneously in the back of the mice. FVIII (20 µg) was mixed with complete Freund's adjuvant for the first injection. In the subsequent immunizations, incomplete Freund's adjuvant was used with same concentration of the antigen. Ten days after the last immunization, eye-blood from mice was screened, using ELISA, for FVIII specific antibodies. Mice with positive serum titres were boosted with 10 µg of the FVIII variant used for initial immunization by intravenous injection and sacrificed after three days. The spleens were removed aseptically and dispersed to a single cell suspension. Fusion of spleen cells and myeloma cells (FOX, X63, SP2/0) was done by the PEG-method or by electrofusion.

Monoclonal antibodies were purified by means of protein A affinity chromatography.

Detection of Stabilizing Anti-FVIIIa Antibodies in Hybridoma Supernatants (Primary Screen)

The ability of anti-FVIIIa antibodies to stabilize FVIIIa was evaluated in a functional chromogenic primary screening assay as follows: 30 µl of anti-FVIII supernatants were transferred to 96-well Spectramax microtiter plates followed by 20 µl of 1.04 nM FVIII. Subsequently, 20 µl of 14 nM thrombin (Roche, Germany) were added and incubated for 5 minutes at room temperature allowing FVIII to be activated. After incubation thrombin was inactivated by adding 20 µl containing 50 ATU/ml hirudin and 162.5 µM 25:75 PS:PC phospholipids (Rossix, Sweden). Activated FVIII was then allowed to dissociate for 7.5 minutes at room temperature followed by quantification of remaining FVIIIa activity. To this end a 40 µl-mixture of 1.3 nM FIXa and 162.5 nM FX (Enzyme Research, USA) was added and incubated for 5 minutes at room temperature followed by addition of 100 µl of the FXa substrate S-2765 at 920 µM (Chromogenix, Sweden). Following 5 min incubation at room temperature 25 µl 1 M citric acid (Merck, Germany), pH 3, were added to stop the reaction. The absorbance at 405 nm was measured on an Envision plate reader (Perkin Elmer, USA) with absorbance at 620 nm used as reference wavelength. Three medium controls were included in the assay: one with no dissociation time (max activity) and two, with a 7.5-min dissociation time (minimum activity) and three, with a 7.5-min dissociation time and with FVIII replaced by buffer (background). The two first control samples defined the assay window and the third control was subtracted from all measurements. The data in FIG. 1 demonstrate the ability of the anti-FVIII supernatants to stabilize FVIII against spontaneous disassociation.

Detection of Stabilizing Anti-FVIIIa Antibodies in Hybridoma Supernatants (Secondary Screen)

Anti-FVIIa supernatants from the primary screen were rescreened in a secondary time course assay to evaluate their effect on FVIIIa decay at several time points and at two antibody concentrations. The assay was performed as follows: 15 or 30 µl of anti-FVIII supernatant were transferred to 96-well Spectramax microtiter plates followed by 20 µl of 1.04 nM FVIII. Thrombin (20 µl of 14 nM; Roche, Germany) was added and incubated for 5 min at room temperature allowing FVIII to be activated. Following activation, thrombin was inactivated by adding 20 µl containing 50 ATU/ml hirudin and 162.5 µM 25:75 PS:PC phospholipids (Rossix, Sweden). Activated FVIII was then allowed to dissociate for 7.5, 15, and 25 min at room temperature. Remaining FVIIIa activity was measured by the addition of a 40 µl-mixture of 1.3 nM FIXa and 162.5 nM FX (Enzyme Research, USA) and incubated for 5 min at room temperature followed by addition of 100 µl 920 µM S-2765 chromogenic FXa substrate S-2765 (Chromogenix, Sweden). Five minutes later 25 µl 1 M citric acid (Merck, Germany), pH 3, were added to stop the reaction. The absorbance at 405 nm was measured on an Envision plate reader (PerkinElmer, USA) with absorbance at 620 nm used as reference wavelength. A medium control was included in the assay to verify the dependence of FVIII in the assay. The control had a dissociation time of 7.5 minutes and buffer was added instead of FVIII.

Figure 2:
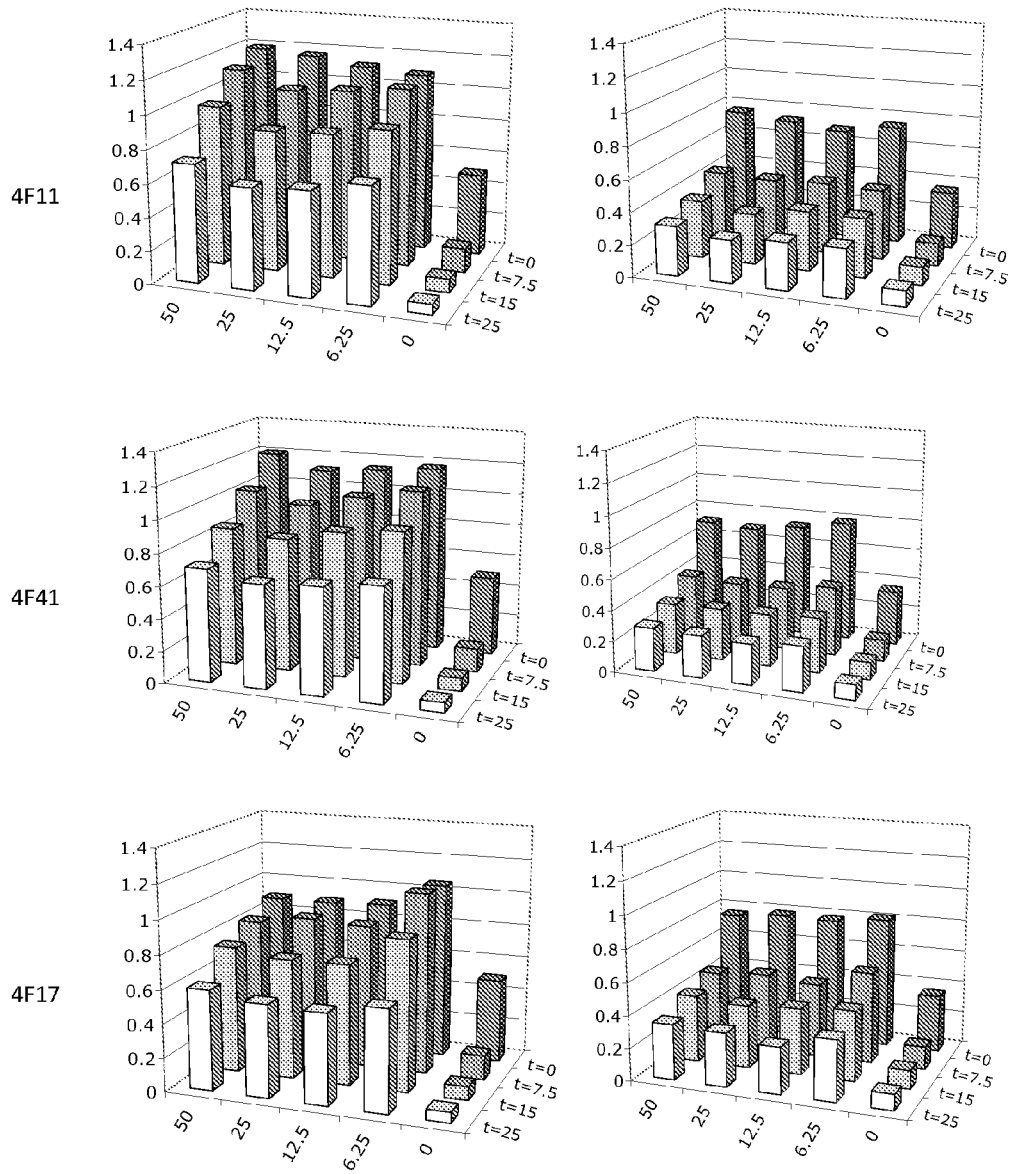
FIG. 2 shows antibodies tested in five different concentrations (0-50 nM) at four different dissociation timepoints (0-25 minutes) with phospholipids added together with FVIII (phospholipid dependent) or with phospholipids added together with FIXa/FX-mix (phospholipid independent). The measured signal (absorbance at 405 nm) is proportional to the remaining FVIIIa activity after dissociation. Comparison of the two reaction conditions demonstrate that the majority of antibodies are able to stabilize FVIIIa in the presence of phospholipid whereas the degree of FVIIIa stabilization in the absence of phospholipid during FVIIIa decay is less. For most antibodies, maximal stabilization of FVIIIa is observed even at the lowest antibody concentration. One exception is 4F136 with less stabilization at the lowest antibody concentrations indicating a relatively low affinity interaction.

Characterization of Purified Anti-FVIII mAbs in Functional Chromogenic Screening Assay Purified anti-FVIIIa antibodies were tested in a time course assay at different concentrations and in the presence or absence of phospholipid to evaluate their effect on the kinetics FVIIIa decay as well as dependence on the presence of phospholipid and antibody concentration. The assay was performed as follows: 30 μl of purified anti-FVIII antibody were transferred to 96-well Spectramax microtiter plates followed by 20 μl of 1.04 nM FVIII (phospholipid independent) or alternatively 20 μl containing 1.04 nM FVIII and 162.5 μM 25:75 PS:PC phospholipids (Rossix, Sweden) (phospholipid dependent). Thrombin (20 μl of 14 nM; Roche, Germany) was added and incubated for 5 min at room temperature allowing FVIII to be activated. After the incubation time thrombin was inactivated by adding 20 μl 50 ATU/ml hirudin. Activated FVIII was then allowed to dissociate for 7.5, 15, 25 minutes at room temperature. Remaining FVIIIa activity was measured by the addition a 40-μl mixture of 1.3 nM FIXa and 162.5 nM FX (Enzyme Research, USA) (phospholipid dependent) or alternative a 40-μl mixture of 1.3 nM FIXa, 162.5 nM FX (Enzyme Research, USA) and 81.25 μM 25:75 PS:PC phospholipids (Rossix, Sweden) (phospholipid in dependent) and incubated for 5 min at room temperature followed by addition of 100 μl 920 μM S-2765 chromogenic FXa substrate (Chromogenix, Sweden). After 5 min at room temperature 25 μl 1 M citric acid (Merck, Germany), pH 3, were added to stop the reaction. The absorbance at 405 nm was measured on an Envision plate reader (PerkinElmer, USA) with absorbance at 620 nm used as reference wavelength. A medium control was included in the assay to verify the dependence of FVIII in the assay. The control had a dissociation time of 7.5 minutes and buffer was added instead of FVIII. The data in FIG. 2 demonstrate the ability of the anti-FVIII supernatants to stabilize FVIII against spontaneous disassociation over incubation times of 7.5, 15, and 25 minutes and that all the observed stabilization effects are FVIII dependent.

Example 2

Epitope Binning of Antibodies

Antibodies were assigned to epitope bins by performing competition binding to FVIII using a tandem blocking assay (Abdiche et al., 2009) on a Biacore 3000 instrument (GE Healtcare, Uppsala, Sweden). The assay consisted of three steps encompassing oriented capture of FVIII on the chip by virtue of a immobilized non-interfering antibody (4F30) recognizing the C2-domain followed by consecutive binding of primary and secondary antibodies each at 200 nM to ensure saturation of FVIII. Overlapping epitopes were observed as an inability of secondary antibodies to bind following primary antibody binding and used to group antibodies into epitope bins.

FVIII capture antibody (4F30) at 50 μg/ml in 10 mM acetate buffer, pH 5.0 was immobilized in flow cells 1 and 2 of a CM5 chip using standard NHS/EDC coupling chemistry as described by the manufacturer (GE Healthcare, Uppsala, Sweden). The final coupling level was 10 kRU. Subsequent binding experiments were performed at 25° C. and a flow rate of 5 μ/min in running buffer (10 mM HEPES, 150 mM NaCl, 5 mM $CaCl_2$, 0.005% Tween 20, pH 7.4) using flow cell 1 for online reference subtraction. FVIII was captured at a level of 400 RU by injecting 4 nM across flow cell 2 for 2 min. This was followed by a 3-min exposure to 200 nM primary antibody inject across both flow cells and finally an identical injection of 200 nM secondary antibody. Regeneration was performed at the end of each binding experiment by a 2-min pulse of 10 mM glycine, pH 2.0. The entire process was repeated for all pairwise permutations of the antibodies listed in Table 1 except for 4F136 which could not be used as primary antibody due to insufficient FVIII affinity.

Based on these cross-competition studies, antibodies could be grouped in two epitope bins denoted class 1 and class 2. Members belonging to class 1 were 4F143, 4F50, 4F140, and 4F136, while class 2 was represented by 4F11, 4F41, and 4F17 (Table 1). No competition between antibodies across the two classes were observed, whereas members within each class were mutually exclusive with respect to FVIII binding indicating partially or completely overlapping epitopes.

TABLE 1

Pairwise blocking results for antibodies binding to immobilized FVIII in a Biacore 3000 instrument. Following capture of FVIII to the chip using an immobilized non-interfering antibody recognizing the C2-domain primary and secondary antibodies were bound consecutively at 200 nM each to ensure FVIII saturation. Antibodies fall in two epitope bins denoted class 1 and class 2. No competition between antibodies across the two classes were observed, whereas members within each class were mutually exclusive with respect to FVIII binding indicating partially or completely overlapping epitopes.

|  |  | Secondary antibody | | | | | | |
|---|---|---|---|---|---|---|---|---|
|  |  | Class 1 | | | | Class 2 | | |
|  |  | 4F143 | 4F50 | 4F140 | 4F136 | 4F11 | 4F41 | 4F17 |
| Primary antibody | 4F143 | C | C | C | C | N | N | N |
|  | 4F50 | C | C | C | C | N | N | N |
|  | 4F140 | C | C | C | C | N | N | N |
|  | 4F136 | — | — | — | — | — | — | — |
|  | 4F11 | N | N | N | N | C | C | C |

TABLE 1-continued

Pairwise blocking results for antibodies binding to immobilized FVIII in a Biacore 3000 instrument. Following capture of FVIII to the chip using an immobilized non-interfering antibody recognizing the C2-domain primary and secondary antibodies were bound consecutively at 200 nM each to ensure FVIII saturation. Antibodies fall in two epitope bins denoted class 1 and class 2. No competition between antibodies across the two classes were observed, whereas members within each class were mutually exclusive with respect to FVIII binding indicating partially or completely overlapping epitopes.

|  | Secondary antibody | | | | | | |
|---|---|---|---|---|---|---|---|
|  | Class 1 | | | | Class 2 | | |
|  | 4F143 | 4F50 | 4F140 | 4F136 | 4F11 | 4F41 | 4F17 |
| 4F41 | N | N | N | N | C | C | C |
| 4F17 | N | N | N | N | C | C | C |

Abbreviations:
'C', competition i.e. no binding of the secondary antibody;
'N', no competition, i.e. binding of the secondary antibody;
'—', not tested due to poor affinity.

Example 3

Affinity for FVIII

The kinetics of FVIII binding to antibody was determined by surface plasmon resonance using a Biacore 3000 instrument. Each antibody was captured to a level of 70-110 RU in flow cell 2 of a CM5 chip coated with rabbit anti-mouse IgG antibody (GE Healthcare, Uppsala, Sweden) as described by the manufacturer. Kinetic analysis was performed at 25° C. at a flow rate of 30 μl/min in running buffer using flow cell 1 as reference. Serial two-fold dilutions of FVIII from 0 to 40 nM were analyzed. Following 3-min equilibration of the flow cells in running buffer, 150 μl FVIII were injected. The dissociation phase lasted 9 min and regeneration was performed with a 3-min pulse of 10 mM glycine, pH 1.7. The obtained reference-subtracted sensorgrams fitted well to a 1:1 Langmuir binding model which allowed for estimation of association ($K_{on}$) and dissociation ($k_{off}$) rate constants and the equilibrium dissociation constant ($K_d = k_{off}/k_{on}$) using BIAevaluation 4.1 software (GE Healthcare, Uppsala, Sweden).

TABLE 2

Surface plasmon resonance analysis of the kinetics of FVIII binding to select antibodies. The listed antibodies were captured by immobilized rabbit anti-mouse IgG antibody and binding to FVIII were tested in concentrations ranging from 0 to 40 nM. Binding curves fitted well to a 1:1 Langmuir binding isotherm which provided estimates of association ($k_{on}$) and dissociation ($k_{off}$) rate constants. The dissociation constant $K_d$ was calculated as $k_{off}/k_{on}$. Standard errors obtained from the fits are shown.

|  | $k_{on}$ ($\times 10^5$ M$^{-1}$s$^{-1}$) | $k_{off}$ ($\times 10^{-4}$ s$^{-1}$) | $K_d$ (nM) |
|---|---|---|---|
| 4F143 | 2.44 ± 0.04 | 8.49 ± 0.02 | 3.5 |
| 4F50 | 1.90 ± 0.06 | 10.60 ± 0.04 | 5.6 |
| 4F140 | 2.41 ± 0.19 | 8.07 ± 0.93 | 3.3 |

Example 4

Stabilization of FVIIIa

The effect of antibody on the spontaneous dissociation of FVIIIa was measured in a functional decay assay essentially as described elsewhere (Fay et al., 1996; Parker et al., 2006). Activation of FVIII (0.36 nM) in a volume of 200 μl was performed by combining with 20 μl human alpha-thrombin (American Diagnostica, Stamford, Conn., USA) to a final thrombin concentration of 40 nM. Following 30 sec of activation, 20 μl recombinant hirudin (300 nM) were added to inhibit thrombin and generated FVIIIa was allowed to decay for defined periods. Residual FVIIIa was quantified by measuring its ability to support conversion of FX into FXa. FVIIIa decay mixture (20 μl) was transferred to 60 μl plasma-derived FIXa (American Diagnostica) containing 25:75 PS:PC phospholipid vesicles (Haematologic Technologies Inc., Essex Junction, Vt., USA) to assemble Xase complexes and following 15 sec incubation 20 μl human plasma-derived FX (Enzyme Research Laboratories, South Bend, Ind., USA) were added. Final concentrations during FX activation were 10 nM (FIXa), 25 μM (phospholipid), and 150 nM (FX), respectively. FX activation was allowed to proceed for 30 sec before the reaction was terminated by dilution into an equal volume of quench buffer (20 mM HEPES, 150 mM NaCl, 200 mM EDTA, 10 mM Triton X-100, pH 7.4) and generated FXa was measured in the presence of 0.4 mM S-2765 chromogenic substrate by measuring the increase in absorbance at 405 nm over time (Chromogenix, Instrumentation Laboratory Company, Bedford, Mass., USA). All experiments were performed at room temperature in 20 mM HEPES, 150 mM NaCl, 5 mM CaCl$_2$, 5 mg/ml BSA, pH 7.4 buffer in 96-well plates (Nunc, Denmark) and with shaking to ensure rapid mixing. Where indicated 10 μM phospholipid and/or 20 nM antibody were added together with FVIII or hirudin, or FVIII was replaced with the variant FVIII S289L which has been shown to spontaneously dissociate approximately 4-fold faster than wt FVIII upon activation (Pipe et al., 2001).

Figure 3:
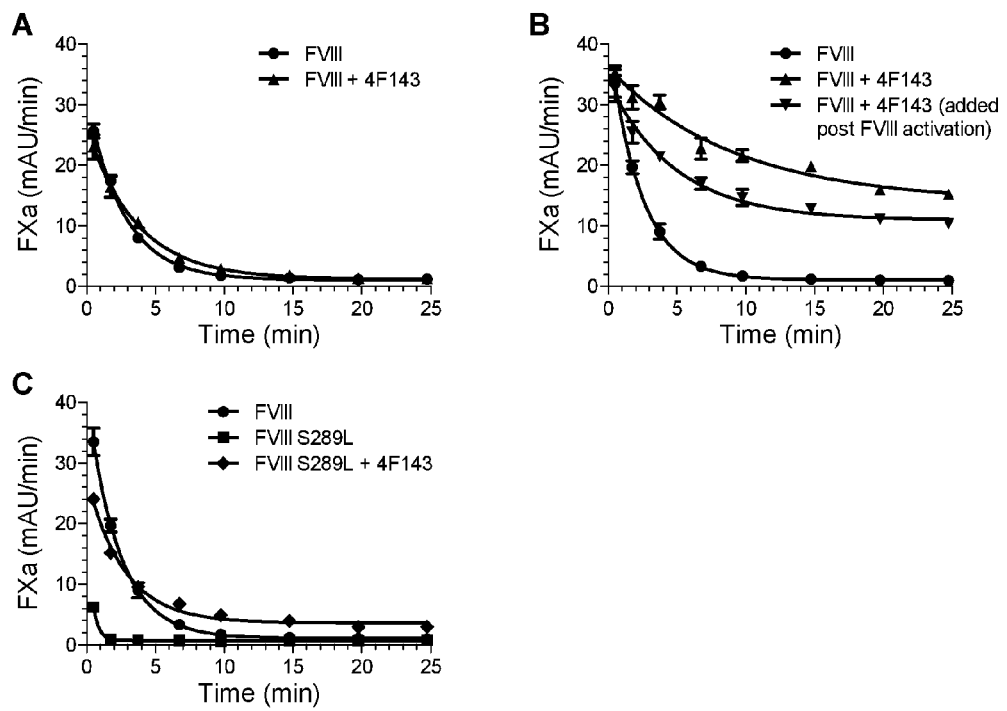
FIG. 3. Effect of 4F143 on the time-dependent spontaneous decay of activated FVIII or FVIII S289L. FVIII at 0.3 nM was rapidly activated with 40 nM thrombin for 30 sec at room temperature and pH 7.4 followed by addition of hirudin to inactivate thrombin. At the indicated time points, the decay mixture was diluted into FIXa/phospholipid and the initial rate of FX activation determined as milli absorbance units at 405 nm per minute (mAU/min). (A) Binding of 4F143 does not stabilize FVIIIa against spontaneous dissociation in the absence of phospholipid. Reactions were performed in the absence of phospholipid and either in the absence (●) or the presence (▲) of 20 nM 4F143 antibody during activation and subsequent decay of FVIIIa. (B) Significant stabilization of FVIIIa by 4F143 in the presence of phospholipid. Stabilization is not dependent on the pre-association of FVIII and antibody before thrombin activation. Reactions were performed in the presence of 10 µM phospholipid during FVIII activation and decay. Symbols indicate (●) No antibody present, (▲) 20 nM 4F143 present during FVIIIa activation and decay, and (▼) 20 nM 4F143 present during FVIIIa decay. (C) 4F143 is able to slow the rate of dissociation of FVIIIa S289L to approximately the level observed for wt FVIIIa in the absence of antibody. Reactions were performed in the presence of 10 µM phospholipid during activation and decay of FVIII or FVIII S289L; (●,■) No antibody present, (♦) 20 nM 4F143 present during FVIII S289L activation and decay.

Results from these experiments (FIG. 3) demonstrate that 4F143 and the other class 1 antibodies slow the rate of spontaneous FVIIIa dissociation by a mechanism that is strictly dependent on the presence of a phospholipid surface. Pre-association of FVIII and antibody before thrombin activation is not required for stabilization. Partial to complete rescue of the FVIII S289L variant is observed. Similar rates of FX activation at the first time point in the presence or absence of antibody indicate that the antibody does not affect the rate of FX conversion to FXa under the chosen experimental conditions.

Example 5

Effect of Antibody on the Interaction of FVIII with vWF

The effect of antibody on the binding of FVIII to von Willebrand factor (vWF) was studied by a solid-phase competition assay in which wells coated with vWF were exposed to FVIII at different added antibody concentrations (Layet et al., 1992; Ganz et al., 1991; Vlot et al., 1995). Nunc MaxiSorp microtiterplate wells (Nunc, Denmark) were coated with 1 μg/ml of vWF (FVIII-free vWF from American Diagnostica) in 20 mM Imidazole, 150 mM NaCl, 10 mM CaCl2, pH 7.3 overnight at 4° C. and then blocked for 1 hour with the same buffer supplemented with 10 mg/ml bovine serum albumin and 0.02% (v/v) Tween 80 (blocking buffer). Coated wells were incubated for 1 hour at room temperature with 100 μl FVIII diluted in blocking buffer to concentrations ranging from 0.05 to 6.4 nM in the presence of 0-162 nM antibody; the highest concentrations significantly exceeding the measured $K_d$ (see Table 2) for the FVIII-antibody interaction. After repeated washing with blocking buffer, 3.33 nM biotinylated monoclonal anti-FVIII antibody 1F5 recognizing the 720-740 region was added in a volume of 100 μl blocking buffer and allowed to incubate for 15 min. Wells were washed and peroxidase-conjugated streptavidin (xx) was added in 100 μl blocking buffer and allowed to bind to residing biotin for 15 min. After repeated washing with blocking buffer, bound FVIII was quantified as the amount of TMB (100 μl TMB Plus, KEM-EN-TEC Diagnostics, Denmark) processed by perioxidase. The reaction was stopped after 5 minutes by the addition of an equal volume of 2 M phosphoric acid and the amount of product formed was quantified by absorbance at 450 nm in a SpectraMax plate reader.

Figure 4:
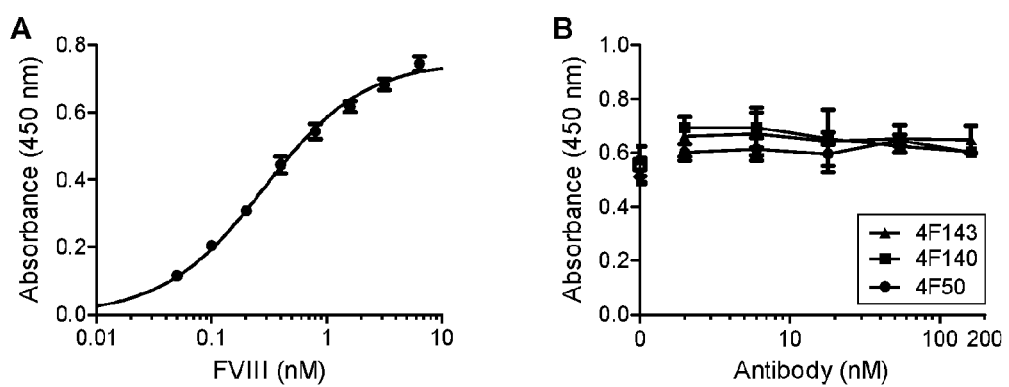
FIG. 4. Effect of antibodies on the binding of FVIII to immobilized vWF in a solid-phase binding assay. (A) Titration of vWF with 0.05 to 6.4 nM FVIII in the absence of antibody. Analysis of data according to a one-site binding model gave an apparent dissociation constant ($K_d$) of 0.29±0.01 nM, which agrees well with published values (Vlot et al., 1995). Results are shown as mean±standard deviation (n=4). (B) The effect of antibody on FVIII binding to vWF was investigated at a single FVIII concentration (0.8 nM) giving half maximal binding to vWF in the absence of antibody. Antibody concentrations ranged from 0 to 162 nM with the highest concentrations being more than one order of magnitude above the measured $K_d$ for the FVIII-antibody interaction (see Table 2). Bound FVIII was detected using an anti-FVIII antibody recognizing a non-overlapping epitope. None of the antibodies tested were found to affect the interaction of FVIII with vWF. Results are shown as mean±standard deviation (n=2).

As shown in FIG. 4 none of the antibodies tested (4F143, 4F140 or 4F50) affected the interaction of FVIII with vWF even at concentrations ensuring essentially complete saturation of FVIII with antibody.

Example 6

Effect of Antibody on the Activation of FVIII by Thrombin

Conversion of FVIII to the activated cofactor occurs by limited proteolysis at three sites in the heavy and light chain catalyzed by thrombin or factor Xa, and with the former most likely representing the physiologic activator (Pieters et al., 1989). Cleavage at R1689 in the light chain liberates the acidic a3 region and causes the dissociation of FVIII from vWF. Cleavage of the heavy chain occurs in the interdomainal regions at the A2-B junction (R740) and the A1-A2 junction (Arg372), respectively. Proteolysis at the latter site is essential for FVIII to gain co-factor activity and can be monitored by the generation of the 50-kDa A1 subunit (Fay, 2004; Nogami et al., 2005). Recently an anti-FVIII antibody was described that accelerated the proteolytic activation of FVIII (Takeyama et al., 2010) (US 20090297503). In addition we find that the well-known monoclonal anti-FVIII antibodies ESH5 and ESH8 originally described by (Griffin et al., 1986) and available from American Diagnostica Inc. (Stamford, Conn., USA) also accelerate FVIII activation by thrombin. To determine the effect of antibodies from the present invention on the kinetics of FVIII activation, a proteolytic assay was used that monitors A1 subunit generation by reversed-phase HPLC. This particular assay was chosen in favor of a traditional functional assays quantifying FVIIIa activity as a function of time to avoid any confounding effects arising from the antibody-mediated stabilization of FVIIIa against spontaneous decay.

Activation of FVIII (100 nM) by 1 nM thrombin (Haematologic Technologies, Essex Junction, Vt., USA) was performed in 20 mM HEPES, 150 mM NaCl, 5 mM CaCl2, 0.01% (v/v) Tween 80, pH 7.4 buffer at 37° C. At defined intervals activation was quenched by addition of 200 nM hirudin. Quenched samples were cooled on ice and then analyzed by rpHPLC to quantify the amount of generated light chain. Time-course studies demonstrated that the addition of hirudin effectively prevented further activation of FVIII.

The FVIII light chain was quantified by injection of 10-20 μl onto a Vydac $C_{18}$ column (3.2×250 mm, 5 μm, 300 Å) in 34% solvent B. Mobile phases consisted of water containing 0.09% (v/v) trifluoroacetic acid (solvent A) and acetonitril containing 0.09% (v/v) trifluoroacetic acid (solvent B). Separation was achieved by a linear gradient from 34 to 65% solvent B over 15 min at a flow rate of 1 ml/min. The column was maintained at 40° C. and eluting FVIIIa subunits were detected and quantified by fluorescence with excitation at 280 nm and emission at 340 nm. Peak areas were converted to molar concentrations based on a standard curve generated by injection of defined amounts of FVIIIa prepared by thrombin activation. The peak representing the A1 subunit was identified from the elution times of the isolated FVIIIa subunits prepared according to published procedures (Lapan and Fay, 1997).

Figure 5:
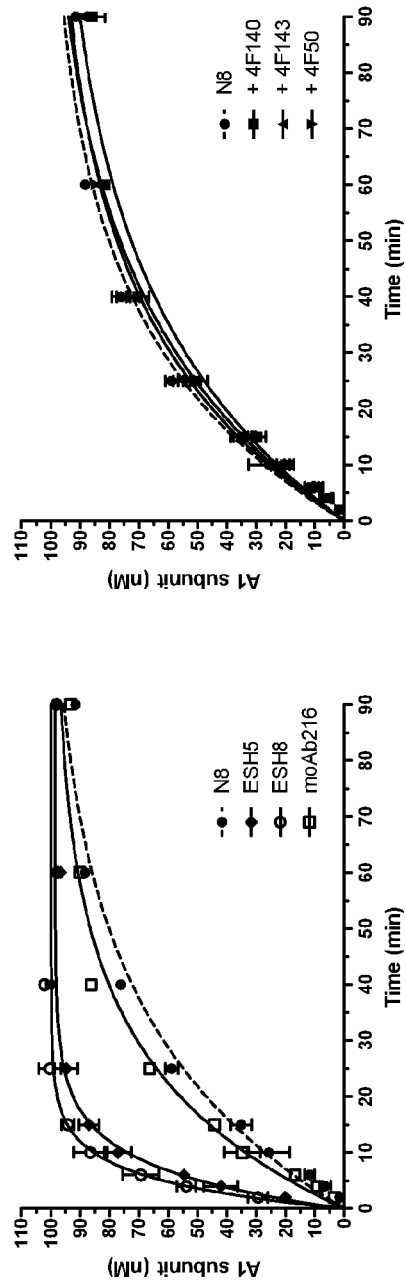
FIG. 5. Effect of antibody on the activation of FVIII by thrombin. Activation of 100 nM FVIII by 1 nM thrombin was performed at 37° C. and in the absence (●, stipled line) or presence of 100 nM ESH5 (♦), ESH8 (○), moAb216 (□), 4F143 (▲), 4F50 (▼), or 4F140 (■). At indicated time points further activation of FVIII was quenched by addition of excess hirudin and the extent of FVIII activation quantified by rpHPLC as the amount of free A1 subunit. ESH5, ESH8, and moAb216 were all found to accelerate the activation of FVIII, whereas no increased rate of activation was observed for 4F143, 4F50, and 4F140.

As demonstrated in FIG. 5, ESH5 and ESH8 (American Diagnostica Inc, Stamford, Conn., USA) were found to accelerate the activation of FVIII by thrombin. Similarly, moAb216 were found to accelerate FVIII activation in agreement with published studies (Takeyama et al., 2010) (US 20090297503), whereas no acceleration was observed for 4F143, 4F50, and 4F140.

Example 7

Effect of Antibody on Thrombin Generation in Haemophilia a Plasma

Washed platelets were prepared as described (Lisman et al., 2005) and added to haemophilia A plasma (George King Bio-Medical Inc) to a final density of 150,000 platelets/μl. Eighty μl of the platelet-containing plasma was mixed with 5 μl relipidated tissue factor (Innovin, Dade, final dilution 1:50000 corresponding to approx 0.12 μM tissue factor) in microtiter wells and preheated 10 min at 37° C. in a Fluoroskan Ascent plate reader (Thermo Electron Corporation). Wild type FVIII or variants (2.7; 0.9, 0.3; 0.1; 0.033; 0.011; 0.0037 and 0.0012 nM final concentration) or wild type FVIII co-formulated with 50 nM 4F143 antibody was added in 15 μl. Fluorogenic substrate (Z-Gly-Gly-Arg-AMC, Bachem, final concentration 417 nM) mixed with $CaCl_2$ (final concentration 16.7 mM) was added in 20 μl before measuring fluorescence (excitation at 390 nm and emission at 460 nm) continuously for one hour. The fluorescence signal was corrected for a2-macroglobulin-bound thrombin activity and converted to thrombin concentration by use of a calibrator and Thrombinoscope software (Synapse BV) as described (Hemker et al., 2003). The maximal level of thrombin activity (Table 3) obtained with 0.011 nM FVIII was measured by the Thrombinoscope software. The maximal rate of thrombin generation was calculated from the parameters obtained from the Thrombinoscope software, as follows: Maximal rate of thrombin generation=maximal level of thrombin activity/ (time to peak thrombin activity−lagtime). Both parameters of thrombin generation show that the antibody 4F143 enhanced the thrombin generation of 0.1 nM FVIII.

TABLE 3

Parameters of thrombin generation obtained by 0.01 nM FVIII with or without 4F143 added. Data for the destabilized FVIII S289L variants are included. The data shows mean ± standard error of the mean (SEM) of 5 individual experiments. Both parameters demonstrate increased thrombin generation when FVIII is combined with 4F143.

| | Rate of thrombin generation | | Maximal level of thrombin generation | |
|---|---|---|---|---|
| | nM/min | fold-increase* | nM | fold-increase* |
| FVIII | 1.2 ± 0.4 | 1 | 29.7 ± 7.0 | 1 |
| FVIII + 4F143 | 2.0 ± 0.9 | 1.8 | 50.3 ± 15.7 | 1.7 |
| FVIII S289L | 0.5 ± 0.1 | 0.39 | 18.0 ± 4.7 | 0.61 |

*compared to FVIII

Example 8

Epitope Mapping by HX-MS of FVIIIa Stabilizing mAbs on FVIII

The HX-MS technology exploits that hydrogen exchange (HX) of a protein can readily be followed by mass spectrometry (MS). By replacing the aqueous solvent containing hydrogen with aqueous solvent containing deuterium, incorporation of a deuterium atom at a given site in a protein will give rise to an increase in mass of 1 Da. This mass increase can be monitored as a function of time by mass spectrometry in quenched samples of the exchange reaction. The deuterium labelling information can be sub-localized to regions in the protein by pepsin digestion under quench conditions and following the mass increase of the resulting peptides.

One use of HX-MS is to probe for sites involved in molecular interactions by identifying regions of reduced hydrogen exchange upon protein-protein complex formation. Usually, binding interfaces will be revealed by marked reductions in hydrogen exchange due to steric exclusion of solvent. Protein-protein complex formation may be detected by HX-MS simply by measuring the total amount of deuterium incorporated in either protein members in the presence and absence of the respective binding partner as a function of time. The HX-MS technique uses the native components, i.e. protein and antibody or Fab fragment, and is performed in solution. Thus HX-MS provides the possibility for mimicking the in vivo conditions (for a recent review on the HX-MS technology, see Wales and Engen, Mass Spectrom. Rev. 25, 158 (2006)).

Instrumentation and Data Recording

All proteins were buffer exchanged into 20 mM Imidazole, 10 mM $CaCl_2$, 150 mM NaCl, adjusted to pH 7.3 before experiments. The HX experiments were automated by a Leap robot (H/D-x PAL; Leap Technologies Inc.) operated by the LeapShell software (Leap Technologies Inc.), which performed initiation of the deuterium exchange reaction, reaction time control, quench reaction, injection onto the UPLC system and digestion time control. The Leap robot was equipped with two temperature controlled stacks maintained at 20° C. for buffer storage and HX reactions and maintained at 2° C. for storage of protein and quench solution, respectively. The Leap robot furthermore contained a cooled Trio VS unit (Leap Technologies Inc.) holding the pepsin-, pre- and analytical columns, and the LC tubing and switching valves at 1° C. The switching valves have been upgraded from HPLC to Microbore UHPLC switch valves (Cheminert, VICI AG). For the inline pepsin digestion, 100 μL quenched sample containing 0.15 pmol FVIII was loaded and passed over a Poroszyme® Immobilized Pepsin Cartridge (2.1×30 mm (Applied Biosystems)) using a isocratic flow rate of 200 μL/min (0.1% formic acid:$CH_3OH$ 95:5). The resulting peptides were trapped and desalted on a VanGuard pre-column BEH C18 1.7 μm (2.1×5 mm (Waters Inc.)). Subsequently, the valves were switched to place the pre-column inline with the analytical column, UPLC-BEH C18 1.7 μm (2.1×100 mm (Waters Inc.)), and the peptides separated using a 9 min gradient of 15-40% B delivered at 150 μL/min from an AQUITY UPLC system (Waters Inc.). The mobile phases consisted of A: 0.1% formic acid in water and B: 0.1% formic acid in $CH_3CN$. The ESI MS data, and the elevated energy ($MS^E$) experiments were acquired in positive ion mode using a Q-T of Premier MS (Waters Inc.). Leucine-enkephalin was used as the lock mass ($[M+H]^+$ ion at m/z 556.2771) and data was collected in continuum mode.

Data Analysis

Peptic peptides were identified in separate experiments using MSE methods (Waters Inc.). MSE data were processed using BiopharmaLynx 1.2 (version 017). HX-MS raw data files were subjected to continuous lockmass-correction. Data analysis, i.e., centroid determination of deuterated peptides and plotting of in-exchange curves, was performed using HX-Express ((Version Beta); Weis et al., J. Am. Soc. Mass Spectrom. 17, 1700 (2006)).

Epitope Mapping of 4F143 and 4F41

Amide hydrogen/deuterium exchange (HX) was initiated by preparation of FVIII solutions in a concentration of 30 μM in the absence or presence of either 4F143 or 4F41 into the corresponding deuterated buffer, i.e., 20 mM Imidazole, 10 mM CaCl2, 150 mM NaCl, prepared in D2O, 98% D2O final, pH 7.3 (uncorrected value)). All HX reactions were carried out at 20° C. and contained 3 μM FVIII in the absence or presence of excess FVIII mAbs (4.5 uM) to ensure saturation of FVIII with antibody. At appropriate time intervals ranging from 10 sec to 2 hours 46 min 40 s (10.000 s), aliquots of the HX reaction were quenched by an equal volume of ice-cold quenching buffer 1.35M TCEP (Tris(2-Carboxyethyl)-Phosphine Hydrochloride (Calbiochem®, EMD Chemicals inc.))) resulting in a final pH of 2.6 (uncorrected value). An example of raw data identifying the 4F143 epitope is shown in FIG. 6A.

4F143 Epitope

Figure 6:
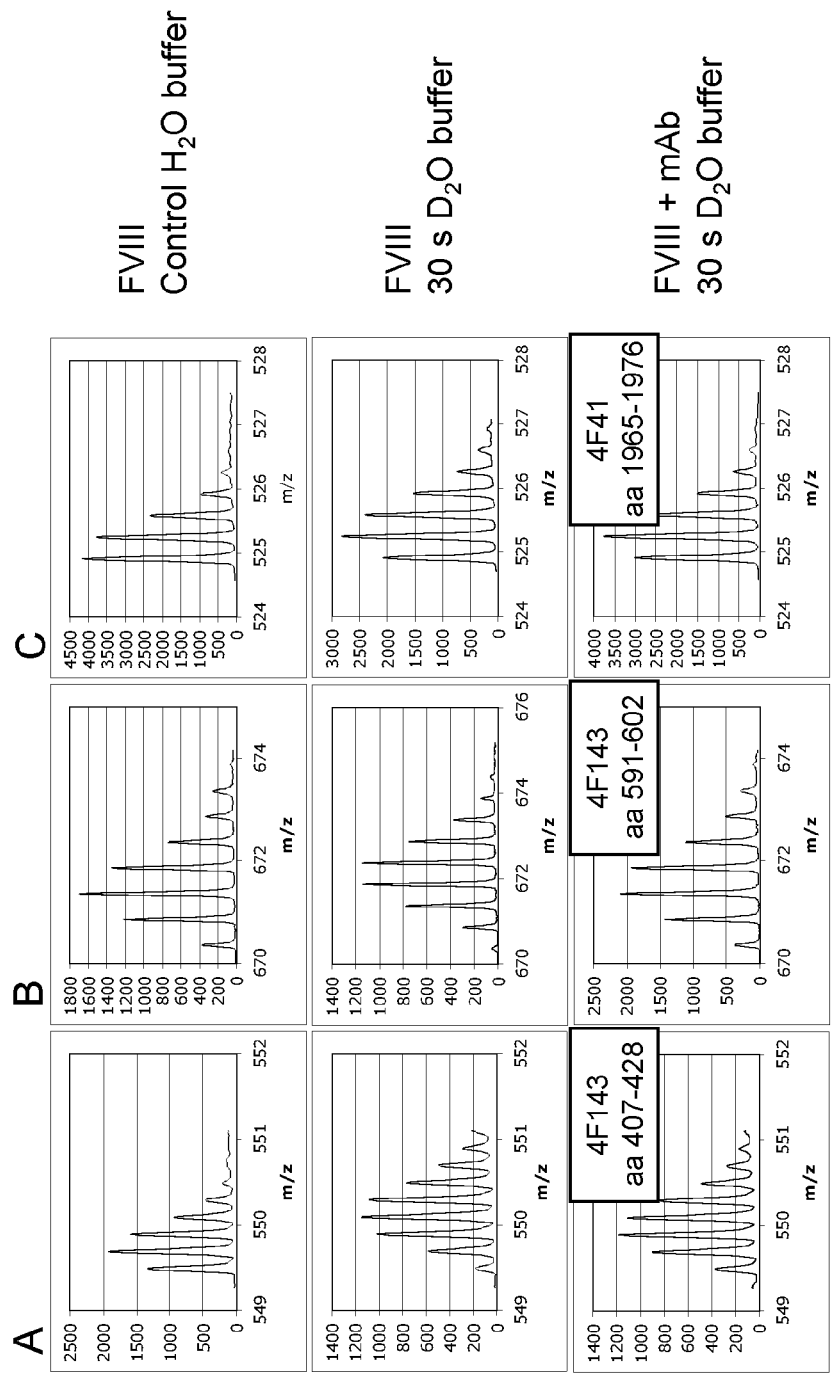
FIG. 6. HX monitored by mass spectrometry identifies regions of FVIII involved in 4F143 and 4F41 binding. (A) Mass/charge spectra corresponding to the peptide fragment aa 407-428 (SEQ ID NO 15), YKSQYLNNGPQRI-GRKYKKVRF ([M+H]+=549.5128, z=5), (B) Mass/charge spectra corresponding to the peptide fragment aa 591-602 (SEQ ID NO 16), IQRFLPNPAGVQ ([M+H]+=670.3730, z=2) both identified to be part of the epitope of 4F143 binding to FVIII. (C) Mass/charge spectra corresponding to the peptide fragment 1965-1976 (SEQ ID NO 17), VRKKEEYK-MALY (m/z=524.9335, z=3), identified to be part of the epitope of 4F41 binding to FVIII. For all spectra the upper panels show the non-deuterated controls, middle and lower panels show the peptide after 30 s in-exchange with D2O in the absence or presence of mAb, respectively.
Figure 7:
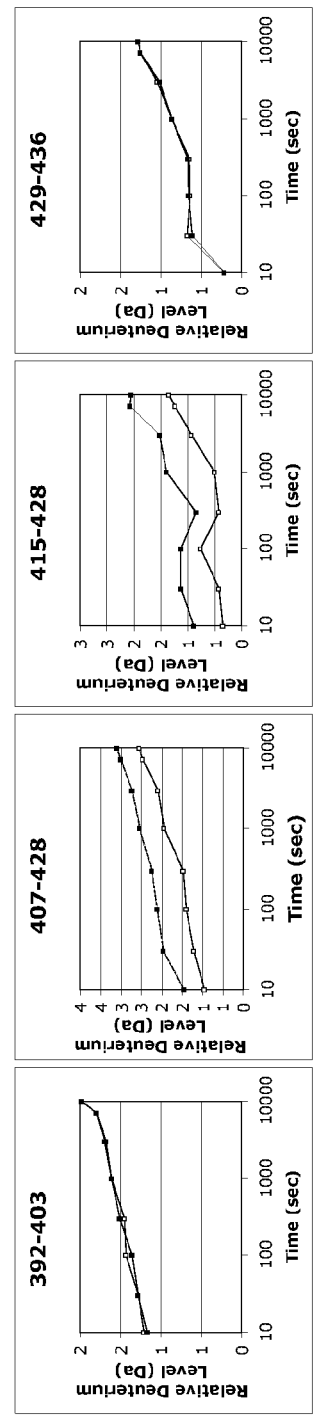
FIG. 7. Hydrogen exchange time-plots of representative peptides of FVIII in the presence of 4F143. Deuterium incorporation (Da) of FVIII peptides is plotted against time on a logarithmic scale in the absence (■) or presence (□) of 4F143. Peptides covering residues aa 392-403 and 429-436 represent regions of FVIII that are unaffected by complex formation with 4F143. Peptides covering residues aa 407-428, and 415-428 represent regions of FVIII that are part of the binding epitope of 4F143.
Figure 8:
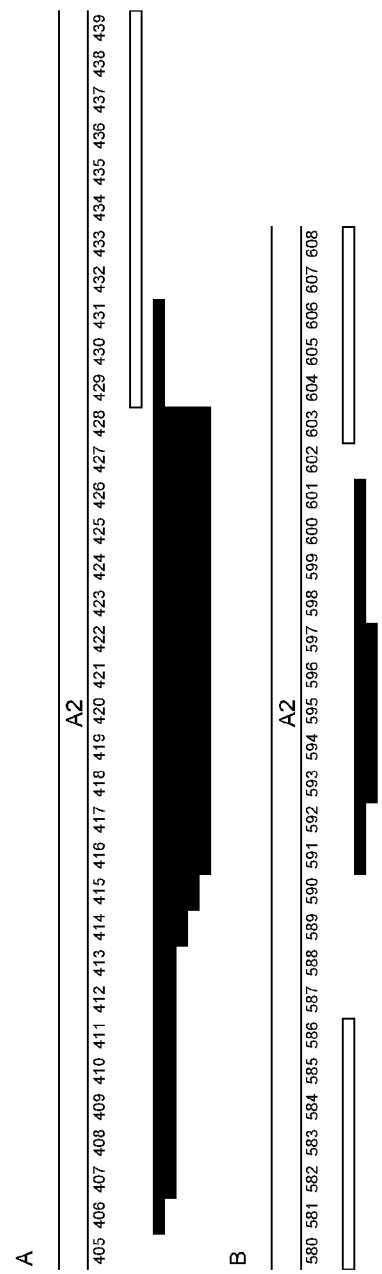
FIG. 8. Sequence coverage of HX analyzed peptides of FVIII in the presence of 4F143. The primary sequence (using mature numbering) is displayed above the HX analyzed peptides (shown as horizontal bars) for both epitope regions identified, i.e., the sequence (A) aa 407-428 and (B) aa 591-602. Peptides showing similar exchange patterns both in the presence and absence of 4F143 are displayed in with no fills (□) whereas peptides showing reduced deuterium incorporation upon 4F143 binding are filled in black (■).

The deuterium incorporation rate (HX time-course) of 412 peptides, covering 82% of the primary sequence of FVIII, were monitored in the presence and absence of 4F143 at 8 time points, i.e., 10 s, 30 s, 100 s, 300 s, 1.000 s, 3,000 s, and 10,000 s (FIG. 6A, FIG. 7, FIG. 8).

The observed exchange pattern in the presence or absence of 4F143 may be divided into two groups: One group of peptides display an exchange pattern that is unaffected by the binding of 4F143 (FIG. 7 (aa 392-403 and 429-436)), which comprises 98.2% of the peptides. In contrast, another group of FVIII peptic peptides show protection from exchange upon complex formation with 4F143 (FIG. 7), which includes 1.7% of the peptic peptides. For example at 30 s exchange with D2O, approximately 1 amide is protected from exchange in the region aa 407-428 upon 4F413 binding (FIG. 6A, FIG. 7). Two regions were found to display protection upon 4F143 binding, one region includes 5 peptic peptides covering the residues aa 407-428, 414-428, 415-428, 416-428 and 406-431, and an additional region includes 2 peptic peptide covering the residues aa 591-602 and 593-597. The two epitope regions are both found within the A2 subdomain of FVIII.

Comparison of the relative amounts of exchange protection by overlapping peptides enabled to narrow the affected regions of FVIII upon complex formation with 4F143 to be found within the sequence aa 407-428 and 591-602 (using mature numbering).

The relative exchange protection rate was determined for the peptic petides included in the two epitopes regions by comparing HX results of free FVIII vs FVIII in complex formation with 4F143.

For the epitope region within the sequence aa 407-428 the relative exchange protection identified for the peptides covering residues aa 414-428, 415-428, 416-428 was found to be at a comparable level and approximately 50% of the relative level determined for the peptides covering residue aa 406-431, 407-428.

For the epitope region within the sequence aa 591-602 the relative exchange protection identified for the peptide covering residues aa 593-597 was found to be approximately 40% of the relative proction level determined for the peptide covering residues aa 591-602.

The two epitope regions covering the sequence aa 407-428 and 591-602 are found to be in structural close proximity when docking onto the published crystal structure of FVIII Ngo, Jacky Chi Ki; Huang, Mingdong; Roth, David A.; Furie, Barbara C.; Furie, Bruce. Crystal Structure of Human Factor VIII: Implications for the Formation of the Factor IXa-Factor VIIIa Complex. Structure (Cambridge, Mass., United States) (2008), 16(4), 597-606.

4F41 Epitope

Figure 9:
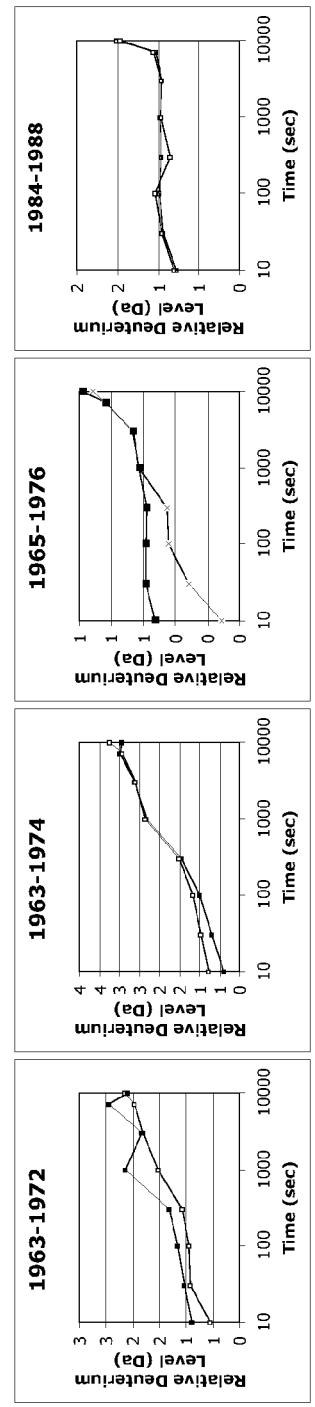
FIG. 9. Hydrogen exchange time-plots of representative peptides of FVIII in the presence of 4F41. Deuterium incorporation (Da) of FVIII peptides is plotted against time on a logarithmic scale in the absence (■) or presence (□) of 4F41. Peptides covering the residues aa 1963-1972, 1963-1974, and 1965-1976 represent regions of FVIII that are part of the binding epitope of 4F41, changes in deuterium exchange rate are observed for short incubation times, i.e., 10 s and 30 s. The peptide covering residues aa 1984-1988 represents regions of FVIII that are unaffected by complex formation with 4F41.
Figure 10:
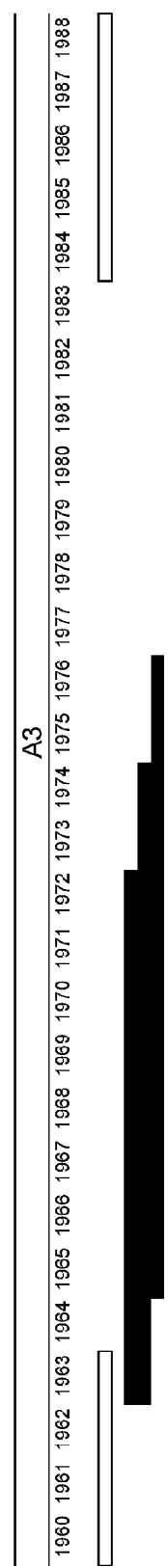
FIG. 10. Sequence coverage of HX analyzed peptides of FVIII in the presence and absence of 4F41. The primary sequence (using mature numbering) is displayed above the HX analyzed peptides (shown as horizontal bars). Peptides showing similar exchange patterns both in the presence and absence of 4F41 are displayed in with no fills (□), and peptides showing reduced deuterium incorporation at short incubation times, i.e., <100 s upon 4F41 binding are filled in black (■).

The HX time-course of 412 peptides, covering 82% of the primary sequence of FVIII, were monitored in the presence and absence 4F41 at 8 time points, i.e., 10 s, 30 s, 100 s, 300 s, 1.000 s, 3.000 s, and 10.000 s (FIG. 6B, FIG. 9, FIG. 10).

The observed exchange pattern in the presence or absence of 4F41 may be divided into two groups; one group of peptides displays an exchange pattern that is unaffected by the binding of 4F41 (FIG. 9), which comprises 99.3% of the peptides; a second group shows protection from exchange upon complex formation with 4F41 (FIG. 9), which includes 0.7% of the peptic peptides.

The study of overlapping peptic peptides enabled the sub-localization of the identified epitope region to be confined within the sequence aa 1965-1970 (using mature numbering), which is found in domain A3 of FVIII. Three peptides were identified to show a significant lowered deuterium incorporation level detectable for short incubation times, i.e., 10 s and 30 s. This clearly indicates them to be situated within the epitope. These peptides covered the sequence aa 1963-1972, 1963-1974, 1965-1976, respectively.

Example 9

Cloning and Sequencing of Mouse Anti-FVIII 4F143 and 4F50 Monoclonal Antibodies

This example describes cloning and sequencing of the murine heavy chain and light chain sequences of anti-FVIII antibody 4F143. Total RNA was extracted from hybridoma cells using the RNeasy-Mini Kit from Qiagen and used as template for cDNA synthesis. cDNA was synthesized in a 5'-RACE reaction using the SMARTer™ RACE cDNA amplification kit from Clontech. Subsequent target amplification of HC and LC sequences was performed by PCR using Phusion Hot Start polymerase (Finnzymes) and the universal primer mix (UPM) included in the SMARTer™ RACE kit as forward primer. A reverse primer with the following sequence was used for HC (VH domain) amplification:

(SEQ ID NO: 3)
5'-CCCTTGACCAGGCATCCCAG-3'

A reverse primer with the following sequence was used for LC amplification:

(SEQ ID NO: 4)
5'-GCTCTAGACTAACACTCATTCCTGTTGAAGCTCTTG-3'

PCR products were separated by gel electrophoresis, extracted using the GFX PCR DNA & Gel Band Purification Kit from GE Healthcare Bio-Sciences and cloned for sequencing using a Zero Blunt TOPO PCR Cloning Kit and chemically competent TOP10 *E. coli* (Invitrogen). Colony PCR was performed on selected colonies using an AmpliTaq Gold Master Mix from Applied Biosystems and M13uni/M13rev primers. Colony PCR clean-up was performed using the ExoSAP-IT enzyme mix (USB). Sequencing was performed at MWG Biotech, Martinsried Germany using M13uni(-21)/M13rev(-29) sequencing primers. Sequences were analyzed and annotated using the Vector NTI program. All kits and reagents were used according to the manufacturer's instructions.

Anti-FVIII 4F143

A single unique murine kappa type LC and a single unique murine HC, subclass IgG1 was identified. Nucleic acid and amino acid sequences are listed below, the leader peptide sequences are not included.

Anti-FVIIIa 4F143 VH amino acid sequence (SEQ ID NO: 5) (signal peptide sequence omitted, CDR1 (SEQ ID NO 6), CDR2 (SEQ ID NO: 7), and CDR3 (SEQ ID NO: 8), respectively, are underlined):

```
  1 QIQFVQSGPE LKKPGETVKI SCKASGYTFT NYGMNWVKQA PGKGLKWMGW

51 INSYTGEPTY ADDFKGRFAF SLETSASTAY LQINNLKNED TATYFCARGA

101 SYAMDYWGQG TSVTVSS
```

Anti-FVIIIa 4F143 VH nucleic acid sequence (SEQ ID NO: 9) (signal peptide sequence omitted):

5'-CAGATCCAGTTCGTGCAGTCTGGACCTGAGCTGAAGAAGCCTGGAGAGACAGTCAAGATCTCCTGCAA

GGCTTCTGGTTATACCTTCACAAACTATGGAATGAACTGGGTGAAGCAGGCTCCAGGAAAGGGTTTAA

AGTGGATGGGCTGGATAAACTCCTACACTGGAGAGCCAACATATGCTGATGACTTCAAGGGACGGTTT

GCCTTCTCTTTGGAAACCTCTGCCAGCACTGCCTATTTGCAGATCAACAACCTCAAAAATGAGGACAC

GGCTACATATTTCTGTGCAAGAGGGGCTTCTTATGCTATGGACTACTGGGGTCAAGGAACCTCAGTCA

CCGTCTCCTCA

Anti-FVIIIa 4F143 VL amino acid sequence (SEQ ID NO: 10) (signal peptide sequence omitted, CDR1 (SEQ ID NO: 11), CDR2 (SEQ ID NO 12), and CDR3 (SEQ ID NO: 13), respectively, are underlined):

```
  1 DVQITQSPSY LAASPGETIT INCRASKSIS KYLAWYQEKP VKTNKLLIYS
 51 GSTLQSGIPS RFSGSGSGTD FTLTISSLEP EDFAMYYCQQ HYEYPLTFGA
101 GTKLELKR
```

Anti-FVIIIa 4F143 VL nucleic acid sequence (signal peptide sequence omitted) (SEQ ID NO: 14):

5'-GATGTCCAGATAACCCAGTCTCCATCTTATCTTGCTGCATCTCCTGGAGAAACCATTACTATTAATTGCAGGGCA

AGTAAGAGCATTAGCAAATATTTAGCCTGGTATCAAGAGAAACCTGTGAAAACTAATAAGCTTCTTATCTACTCT

GGATCCACTTTGCAATCTGGAATTCCATCAAGGTTCAGTGGCAGTGGATCTGGAACAGATTTCACTCTCACCATC

AGTAGCCTGGAGCCTGAAGATTTTGCAATGTATTACTGTCAACAGCATTATGAATACCCGCTCACGTTCGGTGCT

GGGACCAAGCTGGAGCTGAAACGG

Anti-FVIII 4F50

A single unique murine kappa type LC and a single unique murine HC, subclass IgG1 was identified. Nucleic acid and amino acid sequences are listed below, the leader peptide sequences are not included.

Anti-FVIIIa 4F50 VH amino acid sequence (SEQ ID NO: 15) (signal peptide sequence omitted, CDR1 (SEQ ID NO 16), CDR2 (SEQ ID NO: 17), and CDR3 (SEQ ID NO: 18), respectively, are underlined):

```
  1 QIQFVQSGPE LKKPGETVKI SCKASGYTFT NYGMNWVKQA PGKGLKWMGW
 51 INSYTGEPTY ADDFKGRFDF SLETSASTAY LQINNLKNED TATYFCARGA
101 SYAMDHWGQG TSVTVSS
```

Anti-FVIIIa 4F50 VH nucleotide sequence (SEQ ID NO: 19) (signal peptide sequence omitted)

5'-CAGATCCAGTTCGTGCAGTCTGGACCTGAGCTGAAGAAGCCTGGAGAGACAGTCAAGATCTCCTGCAA

GGCTTCTGGTTATACCTTCACAAACTATGGAATGAACTGGGTGAAGCAGGCTCCAGGAAAGGGTTTAA

AGTGGATGGGCTGGATAAACTCCTACACTGGAGAGCCAACATATGCTGATGACTTCAAGGGACGGTTT

GACTTCTCTTTGGAAACCTCTGCCAGCACTGCCTATTTGCAGATCAACAACCTCAAAAATGAGGACAC

GGCTACATATTTCTGTGCAAGAGGGGCTTCTTATGCTATGGACCACTGGGGTCAAGGAACCTCTGTCA

CCGTCTCCTCA

Anti-FVIIIa 4F50 VL amino acid sequence (SEQ ID NO: 20) (signal peptide sequence omitted, CDR1 (SEQ ID NO: 21), CDR2 (SEQ ID NO 22), and CDR3 (SEQ ID NO: 23), respectively, are underlined):

```
  1 DVQITQSPSY LAASPGETIS INCRASKSIS KYLAWYQEKP VKTNKLLIYS

51 GSTLQSGIPS RFSGSGSGTD FTLTISSLEP EDFAMYYCQQ HYEYPLTFGA

101 GTKLELKR
```

Anti-FVIIIa 4F50 VL nucleotide sequence (SEQ ID NO: 24) (signal peptide sequence omitted)

```
5'-GATGTCCAGATAACCCAGTCTCCATCTTATCTTGCTGCATCTCCTGGAGAAACCATTAGTATTAATTG

CAGGGCAAGTAAGAGCATTAGCAAATATTTAGCCTGGTATCAAGAGAAACCTGTGAAAACTAATAAGC

TTCTTATCTACTCTGGATCCACTTTGCAATCTGGAATTCCATCAAGGTTCAGTGGCAGTGGATCTGGA

ACAGATTTCACTCTCACCATCAGTAGCCTGGAGCCTGAAGATTTTGCAATGTATTACTGTCAACAGCA

TTATGAATACCCGCTCACGTTCGGTGCTGGGACCAAGCTGGAGCTGAAACGG
```

REFERENCE LIST

Abdiche, Y. N., Malashock, D. S., Pinkerton, A., and Pons, J. (2009). Exploring blocking assays using Octet, ProteOn, and Biacore biosensors. Anal. Biochem. 386, 172-180.

Fay, P. J. (2004). Activation of factor VIII and mechanisms of cofactor action. Blood Rev 18, 1-15.

Fay, P. J., Beattie, T. L., Regan, L. M., O'Brien, L. M., and Kaufman, R. J. (1996). Model for the factor VIIIa-dependent decay of the intrinsic factor Xase. Role of subunit dissociation and factor IXa-catalyzed proteolysis. J. Biol. Chem. 271, 6027-6032.

Ganz, P. R., Atkins, J. S., Palmer, D. S., Dudani, A. K., Hashemi, S., and Luison, F. (1991). Definition of the affinity of binding between human von Willebrand factor and coagulation factor VIII. Biochem. Biophys. Res. Commun. 180, 231-237.

Griffin, B. D., Micklem, L. R., McCann, M. C., James, K., and Pepper, D. S. (1986). The production and characterisation of a panel of ten murine monoclonal antibodies to human procoagulant factor VIII. Thromb. Haemost. 55, 40-46.

Hemker, H. C., Giesen, P., Al, D. R., Regnault, V., de, S. E., Wagenvoord, R., Lecompte, T., and Beguin, S. (2003). Calibrated automated thrombin generation measurement in clotting plasma. Pathophysiol. Haemost. Thromb. 33, 4-15.

Lapan, K. A. and Fay, P. J. (1997). Localization of a factor X interactive site in the A1 subunit of factor VIIIa. J. Biol. Chem. 272, 2082-2088.

Layet, S., Girma, J. P., Obert, B., Peynaud-Debayle, E., Bihoreau, N., and Meyer, D. (1992). Evidence that a secondary binding and protecting site for factor VIII on von Willebrand factor is highly unlikely. Biochem. J. 282 (Pt 1), 129-137.

Lisman, T., Adelmeijer, J., Cauwenberghs, S., Van Pampus, E. C., Heemskerk, J. W., and De Groot, P. G. (2005). Recombinant factor VIIa enhances platelet adhesion and activation under flow conditions at normal and reduced platelet count. J. Thromb. Haemost. 3, 742-751.

Nogami, K., Zhou, Q., Wakabayashi, H., and Fay, P. J. (2005). Thrombin-catalyzed activation of factor VIII with His substituted for Arg372 at the P1 site. Blood 105, 4362-4368.

Parker, E. T., Doering, C. B., and Lollar, P. (2006). A1 subunit-mediated regulation of thrombin-activated factor VIII A2 subunit dissociation. J. Biol. Chem. 281, 13922-13930.

Pieters, J., Lindhout, T., and Hemker, H. C. (1989). In situ-generated thrombin is the only enzyme that effectively activates factor VIII and factor V in thromboplastin-activated plasma. Blood 74, 1021-1024.

Pipe, S. W., Saenko, E. L., Eickhorst, A. N., Kemball-Cook, G., and Kaufman, R. J. (2001). Hemophilia A mutations associated with 1-stage/2-stage activity discrepancy disrupt protein-protein interactions within the triplicated A domains of thrombin-activated factor VIIIa. Blood 97, 685-691

Rydel, T. J., Ravichandran, K. G., Tulinsky, A., Bode, W., Huber, R., Roitsch, C., and Fenton, J. W. (1990). The structure of a complex of recombinant hirudin and human alpha-thrombin. Science 249, 277-280.

Takeyama, M., Nogami, K., Matsumoto, T., Soeda, T., Suzuki, T., Hattori, K., and Shima, M. (2010). Characterisation of an antibody specific for coagulation factor VIII that enhances facfor VIII activity. Thromb. Haemost. 103, 94-102.

Thim, L., Vandahl, B., Karlsson, J., Klausen, N. K., Pedersen, J., Krogh, T. N., Kjalke, M., Petersen, J. M., Johnsen, L. B., Bolt, G., Norby, P. L., and Steenstrup, T. D. (2010). Purification and characterization of a new recombinant factor VIII (N8). Haemophilia. 16, 349-359.

Vlot, A. J., Koppelman, S. J., van den Berg, M. H., Bouma, B. N., and Sixma, J. J. (1995). The affinity and stoichiometry of binding of human factor VIII to von Willebrand factor. Blood 85, 3150-3157.

The invention claimed is:

1. A method for treating haemophilia A comprising administering, to a patient in need thereof, a monoclonal Factor VIII antibody having the ability to bind to activated Factor VIII, wherein said antibody, upon binding to activated Factor VIII, reduces dissociation of the A2 domain, wherein said antibody does not interfere with von Willebrand Factor (vWF) binding, wherein the light chain of said monoclonal antibody contains CDR1 of SEQ ID NO:11, CDR2 of SEQ ID NO:12, and CDR3 of SEQ ID NO:13, and a heavy chain of said monoclonal antibody contains CDR1 of SEQ ID NO:6, CDR2 of SEQ ID NO:7, and CDR3 of SEQ ID NO:8, and wherein said administration results in improved clot formation.

2. The method according to claim 1, wherein the monoclonal antibody is antibody 4F143 having the VL of SEQ ID NO:10 and the VH of SEQ ID NO:5.

3. The method according to claim 1, wherein the monoclonal antibody is administered parenterally.

4. The method according to claim 1, wherein the monoclonal antibody is administered subcutaneously.

5. The method according to claim 1, wherein the monoclonal antibody is administered in combination with a Factor VIII molecule.

6. The method according to claim 1, wherein the monoclonal antibody is administered as a pharmaceutical composition further comprising pharmaceutically acceptable excipients.

7. A method for treating haemophilia A comprising administering to a patient in need thereof, a monoclonal Factor VIII antibody having the ability to bind to activated human Factor VIII, wherein said antibody, upon binding to activated human Factor VIII, reduces dissociation of the A2 domain, wherein said antibody does not interfere with von Willebrand Factor (vWF) binding, wherein the light chain of said monoclonal antibody contains CDR1 of SEQ ID NO:21, CDR2 of SEQ ID NO:22, and CDR3 of SEQ ID NO:23 and the heavy chain of said monoclonal antibody contains CDR1 of SEQ ID NO:16, CDR2 of SEQ ID NO:17, and CDR3 of SEQ ID NOS:18, and wherein said administration results in improved clot formation.

8. The method according to claim 7 wherein the monoclonal antibody is antibody 4F50 having the VL of SEQ ID NO:20 and the VH of SEQ ID NO:15.

9. The method according to claim 7, wherein the monoclonal antibody is administered parenterally.

10. The method according to claim 7, wherein the monoclonal antibody is administered subcutaneously.

11. The method according to claim 7, wherein the monoclonal antibody is administered in combination with a Factor VIII molecule.

12. The method according to claim 7, wherein the monoclonal antibody is administered as a pharmaceutical composition further comprising pharmaceutically acceptable excipients.

* * * * *

SEQUENCE LISTING

<160> NUMBER OF SEQ ID NOS: 24

<210> SEQ ID NO 1
<211> LENGTH: 2332
<212> TYPE: PRT
<213> ORGANISM: homo sapiens

<400> SEQUENCE: 1

```
Ala Thr Arg Arg Tyr Tyr Leu Gly Ala Val Glu Leu Ser Trp Asp Tyr
 1               5                  10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365
```

-continued

```
Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Val Arg Phe Met Ala Tyr Thr
            420                 425                 430

Asp Glu Thr Phe Lys Thr Arg Glu Ala Ile Gln His Glu Ser Gly Ile
                435                 440                 445

Leu Gly Pro Leu Leu Tyr Gly Glu Val Gly Asp Thr Leu Leu Ile Ile
450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
                740                 745                 750

Gln Lys Gln Phe Asn Ala Thr Thr Ile Pro Glu Asn Asp Ile Glu Lys
            755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
```

-continued

His Gly Leu Ser Leu Ser Asp Leu Gln Glu Ala Lys Tyr Glu Thr Phe
785                 790                 795                 800

Ser Asp Asp Pro Ser Pro Gly Ala Ile Asp Ser Asn Asn Ser Leu Ser
            805                 810                 815

Glu Met Thr His Phe Arg Pro Gln Leu His His Ser Gly Asp Met Val
            820                 825                 830

Phe Thr Pro Glu Ser Gly Leu Gln Leu Arg Leu Asn Glu Lys Leu Gly
            835                 840                 845

Thr Thr Ala Ala Thr Glu Leu Lys Lys Leu Asp Phe Lys Val Ser Ser
850                 855                 860

Thr Ser Asn Asn Leu Ile Ser Thr Ile Pro Ser Asp Asn Leu Ala Ala
865                 870                 875                 880

Gly Thr Asp Asn Thr Ser Ser Leu Gly Pro Pro Ser Met Pro Val His
            885                 890                 895

Tyr Asp Ser Gln Leu Asp Thr Thr Leu Phe Gly Lys Lys Ser Ser Pro
            900                 905                 910

Leu Thr Glu Ser Gly Gly Pro Leu Ser Leu Ser Glu Glu Asn Asn Asp
            915                 920                 925

Ser Lys Leu Leu Glu Ser Gly Leu Met Asn Ser Gln Glu Ser Ser Trp
930                 935                 940

Gly Lys Asn Val Ser Ser Thr Glu Ser Gly Arg Leu Phe Lys Gly Lys
945                 950                 955                 960

Arg Ala His Gly Pro Ala Leu Leu Thr Lys Asp Asn Ala Leu Phe Lys
            965                 970                 975

Val Ser Ile Ser Leu Leu Lys Thr Asn Lys Thr Ser Asn Asn Ser Ala
            980                 985                 990

Thr Asn Arg Lys Thr His Ile Asp Gly Pro Ser Leu Leu Ile Glu
995                 1000                1005

Asn Ser Pro Ser Val Trp Gln Asn Ile Leu Glu Ser Asp Thr Glu
    1010                1015                1020

Phe Lys Lys Val Thr Pro Leu Ile His Asp Arg Met Leu Met Asp
    1025                1030                1035

Lys Asn Ala Thr Ala Leu Arg Leu Asn His Met Ser Asn Lys Thr
    1040                1045                1050

Thr Ser Ser Lys Asn Met Glu Met Val Gln Gln Lys Lys Glu Gly
    1055                1060                1065

Pro Ile Pro Pro Asp Ala Gln Asn Pro Asp Met Ser Phe Phe Lys
    1070                1075                1080

Met Leu Phe Leu Pro Glu Ser Ala Arg Trp Ile Gln Arg Thr His
    1085                1090                1095

Gly Lys Asn Ser Leu Asn Ser Gly Gln Gly Pro Ser Pro Lys Gln
    1100                1105                1110

Leu Val Ser Leu Gly Pro Glu Lys Ser Val Glu Gly Gln Asn Phe
    1115                1120                1125

Leu Ser Glu Lys Asn Lys Val Val Val Gly Lys Gly Glu Phe Thr
    1130                1135                1140

Lys Asp Val Gly Leu Lys Glu Met Val Phe Pro Ser Ser Arg Asn
    1145                1150                1155

Leu Phe Leu Thr Asn Leu Asp Asn Leu His Glu Asn Asn Thr His
    1160                1165                1170

Asn Gln Glu Lys Lys Ile Gln Glu Glu Ile Glu Lys Lys Glu Thr
    1175                1180                1185

1190                1195                1200

```
Leu Ile Gln Glu Asn Val Val Leu Pro Gln Ile His Thr Val Thr
1205                1210                1215

Gly Thr Lys Asn Phe Met Lys Asn Leu Phe Leu Leu Ser Thr Arg
1220                1225                1230

Gln Asn Val Glu Gly Ser Tyr Asp Gly Ala Tyr Ala Pro Val Leu
1235                1240                1245

Gln Asp Phe Arg Ser Leu Asn Asp Ser Thr Asn Arg Thr Lys Lys
1250                1255                1260

His Thr Ala His Phe Ser Lys Lys Gly Glu Glu Glu Asn Leu Glu
1265                1270                1275

Gly Leu Gly Asn Gln Thr Lys Gln Ile Val Glu Lys Tyr Ala Cys
1280                1285                1290

Thr Thr Arg Ile Ser Pro Asn Thr Ser Gln Gln Asn Phe Val Thr
1295                1300                1305

Gln Arg Ser Lys Arg Ala Leu Lys Gln Phe Arg Leu Pro Leu Glu
1310                1315                1320

Glu Thr Glu Leu Glu Lys Arg Ile Ile Val Asp Asp Thr Ser Thr
1325                1330                1335

Gln Trp Ser Lys Asn Met Lys His Leu Thr Pro Ser Thr Leu Thr
1340                1345                1350

Gln Ile Asp Tyr Asn Glu Lys Glu Lys Gly Ala Ile Thr Gln Ser
1355                1360                1365

Pro Leu Ser Asp Cys Leu Thr Arg Ser His Ser Ile Pro Gln Ala
1370                1375                1380

Asn Arg Ser Pro Leu Pro Ile Ala Lys Val Ser Ser Phe Pro Ser
1385                1390                1395

Ile Arg Pro Ile Tyr Leu Thr Arg Val Leu Phe Gln Asp Asn Ser
1400                1405                1410

Ser His Leu Pro Ala Ala Ser Tyr Arg Lys Lys Asp Ser Gly Val
1415                1420                1425

Gln Glu Ser Ser His Phe Leu Gln Gly Ala Lys Lys Asn Asn Leu
1430                1435                1440

Ser Leu Ala Ile Leu Thr Leu Glu Met Thr Gly Asp Gln Arg Glu
1445                1450                1455

Val Gly Ser Leu Gly Thr Ser Ala Thr Asn Ser Val Thr Tyr Lys
1460                1465                1470

Lys Val Glu Asn Thr Val Leu Pro Lys Pro Asp Leu Pro Lys Thr
1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
1580                1585                1590
```

-continued

```
Lys Lys Asp Thr Ile Leu Ser Leu Asn Ala Cys Glu Ser Asn His
1595                1600                1605

Ala Ile Ala Ala Ile Asn Glu Gly Gln Asn Lys Pro Glu Ile Glu
1610                1615                1620

Val Thr Trp Ala Lys Gln Gly Arg Thr Glu Arg Leu Cys Ser Gln
1625                1630                1635

Asn Pro Pro Val Leu Lys Arg His Gln Arg Glu Ile Thr Arg Thr
1640                1645                1650

Thr Leu Gln Ser Asp Gln Glu Glu Ile Asp Tyr Asp Asp Thr Ile
1655                1660                1665

Ser Val Glu Met Lys Lys Glu Asp Phe Asp Ile Tyr Asp Glu Asp
1670                1675                1680

Glu Asn Gln Ser Pro Arg Ser Phe Gln Lys Lys Thr Arg His Tyr
1685                1690                1695

Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860

Asn Pro Ala His Gly Arg Gln Val Thr Val Gln Glu Phe Ala Leu
1865                1870                1875

Phe Phe Thr Ile Phe Asp Glu Thr Lys Ser Trp Tyr Phe Thr Glu
1880                1885                1890

Asn Met Glu Arg Asn Cys Arg Ala Pro Cys Asn Ile Gln Met Glu
1895                1900                1905

Asp Pro Thr Phe Lys Glu Asn Tyr Arg Phe His Ala Ile Asn Gly
1910                1915                1920

Tyr Ile Met Asp Thr Leu Pro Gly Leu Val Met Ala Gln Asp Gln
1925                1930                1935

Arg Ile Arg Trp Tyr Leu Leu Ser Met Gly Ser Asn Glu Asn Ile
1940                1945                1950

His Ser Ile His Phe Ser Gly His Val Phe Thr Val Arg Lys Lys
1955                1960                1965

Glu Glu Tyr Lys Met Ala Leu Tyr Asn Leu Tyr Pro Gly Val Phe
1970                1975                1980

Glu Thr Val Glu Met Leu Pro Ser Lys Ala Gly Ile Trp Arg Val
```

```
                1985                1990                1995
Glu Cys Leu Ile Gly Glu His Leu His Ala Gly Met Ser Thr Leu
        2000                2005                2010

Phe Leu Val Tyr Ser Asn Lys Cys Gln Thr Pro Leu Gly Met Ala
        2015                2020                2025

Ser Gly His Ile Arg Asp Phe Gln Ile Thr Ala Ser Gly Gln Tyr
        2030                2035                2040

Gly Gln Trp Ala Pro Lys Leu Ala Arg Leu His Tyr Ser Gly Ser
        2045                2050                2055

Ile Asn Ala Trp Ser Thr Lys Glu Pro Phe Ser Trp Ile Lys Val
        2060                2065                2070

Asp Leu Leu Ala Pro Met Ile Ile His Gly Ile Lys Thr Gln Gly
        2075                2080                2085

Ala Arg Gln Lys Phe Ser Ser Leu Tyr Ile Ser Gln Phe Ile Ile
        2090                2095                2100

Met Tyr Ser Leu Asp Gly Lys Lys Trp Gln Thr Tyr Arg Gly Asn
        2105                2110                2115

Ser Thr Gly Thr Leu Met Val Phe Phe Gly Asn Val Asp Ser Ser
        2120                2125                2130

Gly Ile Lys His Asn Ile Phe Asn Pro Pro Ile Ile Ala Arg Tyr
        2135                2140                2145

Ile Arg Leu His Pro Thr His Tyr Ser Ile Arg Ser Thr Leu Arg
        2150                2155                2160

Met Glu Leu Met Gly Cys Asp Leu Asn Ser Cys Ser Met Pro Leu
        2165                2170                2175

Gly Met Glu Ser Lys Ala Ile Ser Asp Ala Gln Ile Thr Ala Ser
        2180                2185                2190

Ser Tyr Phe Thr Asn Met Phe Ala Thr Trp Ser Pro Ser Lys Ala
        2195                2200                2205

Arg Leu His Leu Gln Gly Arg Ser Asn Ala Trp Arg Pro Gln Val
        2210                2215                2220

Asn Asn Pro Lys Glu Trp Leu Gln Val Asp Phe Gln Lys Thr Met
        2225                2230                2235

Lys Val Thr Gly Val Thr Thr Gln Gly Val Lys Ser Leu Leu Thr
        2240                2245                2250

Ser Met Tyr Val Lys Glu Phe Leu Ile Ser Ser Ser Gln Asp Gly
        2255                2260                2265

His Gln Trp Thr Leu Phe Phe Gln Asn Gly Lys Val Lys Val Phe
        2270                2275                2280

Gln Gly Asn Gln Asp Ser Phe Thr Pro Val Val Asn Ser Leu Asp
        2285                2290                2295

Pro Pro Leu Leu Thr Arg Tyr Leu Arg Ile His Pro Gln Ser Trp
        2300                2305                2310

Val His Gln Ile Ala Leu Arg Met Glu Val Leu Gly Cys Glu Ala
        2315                2320                2325

Gln Asp Leu Tyr
        2330

<210> SEQ ID NO 2
<211> LENGTH: 21
<212> TYPE: PRT
<213> ORGANISM: ARTIFICIAL
<220> FEATURE:
<223> OTHER INFORMATION: Amino acid sequence of truncated FVIII B domain
      in "N8"
```

<400> SEQUENCE: 2

Ser Phe Ser Gln Asn Ser Arg His Pro Ser Gln Asn Pro Pro Val Leu
1               5                   10                  15

Lys Arg His Gln Arg
            20

<210> SEQ ID NO 3
<211> LENGTH: 20
<212> TYPE: DNA
<213> ORGANISM: artificial
<220> FEATURE:
<223> OTHER INFORMATION: primer

<400> SEQUENCE: 3
cccttgacca ggcatcccag                                           20

<210> SEQ ID NO 4
<211> LENGTH: 36
<212> TYPE: DNA
<213> ORGANISM: artificial
<220> FEATURE:
<223> OTHER INFORMATION: Primer

<400> SEQUENCE: 4
gctctagact aacactcatt cctgttgaag ctcttg                         36

<210> SEQ ID NO 5
<211> LENGTH: 117
<212> TYPE: PRT
<213> ORGANISM: artificial
<220> FEATURE:
<223> OTHER INFORMATION: 4F143 VH amino acid sequence

<400> SEQUENCE: 5

Gln Ile Gln Phe Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Ser Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Ala Ser Tyr Ala Met Asp Tyr Trp Gly Gln Gly Thr Ser
            100                 105                 110

Val Thr Val Ser Ser
        115

<210> SEQ ID NO 6
<211> LENGTH: 5
<212> TYPE: PRT
<213> ORGANISM: artificial
<220> FEATURE:
<223> OTHER INFORMATION: 4F143 CDR1 amino acid sequence

<400> SEQUENCE: 6

Asn Tyr Gly Met Asn
1               5

```
<210> SEQ ID NO 7
<211> LENGTH: 17
<212> TYPE: PRT
<213> ORGANISM: artificial
<220> FEATURE:
<223> OTHER INFORMATION: 4F143 CDR2 amino acid sequence

<400> SEQUENCE: 7

Trp Ile Asn Ser Tyr Thr Gly Glu Pro Thr Tyr Ala Asp Asp Phe Lys
1               5                   10                  15

Gly

<210> SEQ ID NO 8
<211> LENGTH: 8
<212> TYPE: PRT
<213> ORGANISM: artificial
<220> FEATURE:
<223> OTHER INFORMATION: 4F143 CDR3 amino acid sequence

<400> SEQUENCE: 8

Gly Ala Ser Tyr Ala Met Asp Tyr
1               5

<210> SEQ ID NO 9
<211> LENGTH: 351
<212> TYPE: DNA
<213> ORGANISM: artificial
<220> FEATURE:
<223> OTHER INFORMATION: 4F143 VH DNA sequence

<400> SEQUENCE: 9
cagatccagt tcgtgcagtc tggacctgag ctgaagaagc ctggagagac agtcaagatc      60
tcctgcaagg cttctggtta taccttcaca aactatggaa tgaactgggt gaagcaggct     120
ccaggaaagg gtttaaagtg gatgggctgg ataaactcct acactggaga gccaacatat     180
gctgatgact tcaagggacg gtttgccttc tctttggaaa cctctgccag cactgcctat     240
ttgcagatca caaacctcaa aaatgaggac acggctacat atttctgtgc aagagggggct    300 tcttatgcta tggactactg gggtcaagga acctcagtca ccgtctcctc a              351

<210> SEQ ID NO 10
<211> LENGTH: 108
<212> TYPE: PRT
<213> ORGANISM: artificial
<220> FEATURE:
<223> OTHER INFORMATION: 4F143 VL amino acid sequence

<400> SEQUENCE: 10

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Val Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Tyr Glu Tyr Pro Leu
                85                  90                  95
```

Thr Phe Gly Ala Gly Thr Lys Leu Glu Leu Lys Arg
                100                 105

<210> SEQ ID NO 11
<211> LENGTH: 11
<212> TYPE: PRT
<213> ORGANISM: artificial
<220> FEATURE:
<223> OTHER INFORMATION: 4F143 CDR1 amino acid sequence

<400> SEQUENCE: 11

Arg Ala Ser Lys Ser Ile Ser Lys Tyr Leu Ala
1               5                   10

<210> SEQ ID NO 12
<211> LENGTH: 7
<212> TYPE: PRT
<213> ORGANISM: artificial
<220> FEATURE:
<223> OTHER INFORMATION: 4F143 CDR2 amino acid sequence

<400> SEQUENCE: 12

Ser Gly Ser Thr Leu Gln Ser
1               5

<210> SEQ ID NO 13
<211> LENGTH: 9
<212> TYPE: PRT
<213> ORGANISM: artificial
<220> FEATURE:
<223> OTHER INFORMATION: 4F143 CDR3

<400> SEQUENCE: 13

Gln Gln His Tyr Glu Tyr Pro Leu Thr
1               5

<210> SEQ ID NO 14
<211> LENGTH: 324
<212> TYPE: DNA
<213> ORGANISM: artificial
<220> FEATURE:
<223> OTHER INFORMATION: 4F143 VL DNA sequence

<400> SEQUENCE: 14
gatgtccaga taacccagtc tccatcttat cttgctgcat ctcctggaga aaccattact    60
attaattgca gggcaagtaa gagcattagc aaatatttag cctggtatca agagaaacct   120
gtgaaaacta ataagcttct tatctactct ggatccactt tgcaatctgg aattccatca   180
aggttcagtg gcagtggatc tggaacagat ttcactctca ccatcagtag cctggagcct   240
gaagattttg caatgtatta ctgtcaacag cattatgaat acccgctcac gttcggtgct   300
gggaccaagc tggagctgaa acgg                                          324

<210> SEQ ID NO 15
<211> LENGTH: 117
<212> TYPE: PRT
<213> ORGANISM: artificial
<220> FEATURE:
<223> OTHER INFORMATION: 4F50 VH amino acid sequence

<400> SEQUENCE: 15

Gln Ile Gln Phe Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

```
Gly Met Asn Trp Val Lys Gln Ala Pro Gly Lys Gly Leu Lys Trp Met
        35                  40                  45

Gly Trp Ile Asn Ser Tyr Thr Gly Glu Pro Thr Tyr Ala Asp Asp Phe
    50                  55                  60

Lys Gly Arg Phe Asp Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Ala Ser Tyr Ala Met Asp His Trp Gly Gln Gly Thr Ser
            100                 105                 110

Val Thr Val Ser Ser
        115

<210> SEQ ID NO 16
<211> LENGTH: 5
<212> TYPE: PRT
<213> ORGANISM: artificial
<220> FEATURE:
<223> OTHER INFORMATION: 4F50 VH CDR1 amino acid sequence

<400> SEQUENCE: 16

Asn Tyr Gly Met Asn
1               5

<210> SEQ ID NO 17
<211> LENGTH: 16
<212> TYPE: PRT
<213> ORGANISM: artificial
<220> FEATURE:
<223> OTHER INFORMATION: 4F50 VH CDR2 amino acid sequence

<400> SEQUENCE: 17

Ile Asn Ser Tyr Thr Gly Glu Pro Thr Tyr Ala Asp Asp Phe Lys Gly
1               5                   10                  15

<210> SEQ ID NO 18
<211> LENGTH: 8
<212> TYPE: PRT
<213> ORGANISM: artificial
<220> FEATURE:
<223> OTHER INFORMATION: 4F50 VH CDR3

<400> SEQUENCE: 18

Gly Ala Ser Tyr Ala Met Asp His
1               5

<210> SEQ ID NO 19
<211> LENGTH: 351
<212> TYPE: DNA
<213> ORGANISM: artificial
<220> FEATURE:
<223> OTHER INFORMATION: 4F50 VH DNA sequence

<400> SEQUENCE: 19
cagatccagt tcgtgcagtc tggacctgag ctgaagaagc ctggagagac agtcaagatc    60
tcctgcaagg cttctggtta taccttcaca aactatggaa tgaactgggt gaagcaggct   120
ccaggaaagg gtttaaagtg gatgggctgg ataaactcct acactggaga gccaacatat   180
gctgatgact caagggacg gtttgacttc tctttggaaa cctctgccag cactgcctat   240
ttgcagatca caaacctcaa aaatgaggac acggctacat atttctgtgc aagaggggct   300
tcttatgcta tggaccactg gggtcaagga acctctgtca ccgtctcctc a            351
```

```
<210> SEQ ID NO 20
<211> LENGTH: 108
<212> TYPE: PRT
<213> ORGANISM: artificial
<220> FEATURE:
<223> OTHER INFORMATION: 4F50 VL amino acid sequence

<400> SEQUENCE: 20

Asp Val Gln Ile Thr Gln Ser Pro Ser Tyr Leu Ala Ala Ser Pro Gly
1               5                   10                  15

Glu Thr Ile Ser Ile Asn Cys Arg Ala Ser Lys Ser Ile Ser Lys Tyr
            20                  25                  30

Leu Ala Trp Tyr Gln Glu Lys Pro Val Lys Thr Asn Lys Leu Leu Ile
        35                  40                  45

Tyr Ser Gly Ser Thr Leu Gln Ser Gly Ile Pro Ser Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Tyr Glu Tyr Pro Leu
                85                  90                  95

Thr Phe Gly Ala Gly Thr Lys Leu Glu Leu Lys Arg
            100                 105

<210> SEQ ID NO 21
<211> LENGTH: 11
<212> TYPE: PRT
<213> ORGANISM: artificial
<220> FEATURE:
<223> OTHER INFORMATION: 4F50 VL CDR1

<400> SEQUENCE: 21

Arg Ala Ser Lys Ser Ile Ser Lys Tyr Leu Ala
1               5                   10

<210> SEQ ID NO 22
<211> LENGTH: 9
<212> TYPE: PRT
<213> ORGANISM: artificial
<220> FEATURE:
<223> OTHER INFORMATION: 4F50 VL CDR2 amino acid sequence

<400> SEQUENCE: 22

Gln Gln His Tyr Glu Tyr Pro Leu Thr
1               5

<210> SEQ ID NO 23
<211> LENGTH: 9
<212> TYPE: PRT
<213> ORGANISM: artificial
<220> FEATURE:
<223> OTHER INFORMATION: 4F50 VL CDR3

<400> SEQUENCE: 23

Gln Gln His Tyr Glu Tyr Pro Leu Thr
1               5

<210> SEQ ID NO 24
<211> LENGTH: 324
<212> TYPE: DNA
<213> ORGANISM: artificial
<220> FEATURE:
<223> OTHER INFORMATION: 4F50 VL CDR3 amino acid sequence
```

```
<400> SEQUENCE: 24
gatgtccaga taacccagtc tccatcttat cttgctgcat ctcctggaga aaccattagt        60
attaattgca gggcaagtaa gagcattagc aaatatttag cctggtatca agagaaacct       120
gtgaaaacta ataagcttct tatctactct ggatccactt tgcaatctgg aattccatca       180
aggttcagtg gcagtggatc tggaacagat ttcactctca ccatcagtag cctggagcct       240
gaagattttg caatgtatta ctgtcaacag cattatgaat acccgctcac gttcggtgct       300
gggaccaagc tggagctgaa acgg                                              324
```